(12) United States Patent
Yodfat et al.

(10) Patent No.: US 9,162,025 B2
(45) Date of Patent: *Oct. 20, 2015

(54) COLLAPSIBLE RESERVOIR FOR USE WITH A DELIVERY DEVICE

(71) Applicant: Roche Diagnostics Operations, Inc., Indianapolis, IN (US)

(72) Inventors: Ofer Yodfat, Maccabim-Reut (IL); Avraham Neta, Gilon (IL); Doron Bushi, Holon (IL)

(73) Assignee: Roche Diabetes Care, Inc., Indianapolis, IN (US)

( * ) Notice: Subject to any disclaimer, the term of this patent is extended or adjusted under 35 U.S.C. 154(b) by 106 days.

This patent is subject to a terminal disclaimer.

(21) Appl. No.: 13/947,825

(22) Filed: Jul. 22, 2013

(65) Prior Publication Data

US 2013/0310800 A1    Nov. 21, 2013

Related U.S. Application Data

(63) Continuation of application No. 12/452,693, filed as application No. PCT/IL2008/000998 on Jul. 20, 2008, now Pat. No. 8,491,565.

(60) Provisional application No. 60/961,528, filed on Jul. 20, 2007, provisional application No. 60/961,484, filed on Jul. 20, 2007, provisional application No. 60/961,382, filed on Jul. 20, 2007.

(51) Int. Cl.
*A61M 1/00* (2006.01)
*A61M 5/142* (2006.01)
(Continued)

(52) U.S. Cl.
CPC ............ *A61M 5/142* (2013.01); *A61B 5/14532* (2013.01); *A61M 5/14248* (2013.01);
(Continued)

(58) Field of Classification Search
CPC ............... A61M 2005/14264; A61M 5/14248; A61M 5/142; A61M 1/1039; A61M 2205/82; A61M 2205/50; A61M 2005/14204; A61M 5/1723; A61M 5/14532; A61M 5/1486

USPC .................. 604/151, 131, 132, 133, 500, 153
See application file for complete search history.

(56) References Cited

U.S. PATENT DOCUMENTS 3,631,847 A    1/1972   Hobbs, II
3,771,694 A    11/1973  Kaminski
(Continued)

FOREIGN PATENT DOCUMENTS

EP         1002512 A2     5/2000
WO     WO-02085280 A2    10/2002
(Continued)

OTHER PUBLICATIONS

Hirsch, "Evidence-Based Priming", *Diabetes Tech. Therapeutics*, 8(5):521-522 (2006).
(Continued)

*Primary Examiner* — Bhisma Mehta
*Assistant Examiner* — Hamza Darb
(74) *Attorney, Agent, or Firm* — Dinsmore & Shohl LLP

(57) ABSTRACT

Disclosed is a therapeutic fluid reservoir to be used with an ambulatory portable infusion device. The reservoir includes a pliable shell defining a varying inner volume that varies based on the volume of therapeutic fluid held inside the reservoir, the varying inner volume having a predetermined maximum volume for containing a corresponding volume of therapeutic fluid and an outlet port for communicating fluid from the reservoir to a patient, the varying inner volume decreasing upon therapeutic fluid being communicated through the outlet port. Upon the reservoir reaching the predetermined maximum volume when being filled with therapeutic fluid, any therapeutic fluid in excess of the predetermined maximum volume driven into the reservoir causes a substantially corresponding amount of therapeutic fluid to exit out of the reservoir via the outlet port and/or at least one other port provided in the pliable shell.

29 Claims, 25 Drawing Sheets

(51) Int. Cl.
*A61B 5/145* (2006.01)
*A61B 5/1486* (2006.01)
*A61M 5/172* (2006.01)

(52) U.S. Cl.
CPC ............ *A61B5/1486* (2013.01); *A61M 5/1723* (2013.01); *A61M 2005/14204* (2013.01); *A61M 2005/14264* (2013.01); *A61M 2205/50* (2013.01); *A61M 2205/82* (2013.01); *A61M 2207/00* (2013.01)

(56) References Cited

U.S. PATENT DOCUMENTS

| | | | |
|---|---|---|---|
| 4,194,041 | A | 3/1980 | Gore et al. |
| 4,498,843 | A | 2/1985 | Schneider et al. |
| 4,544,369 | A | 10/1985 | Skakoon et al. |
| 4,657,486 | A | 4/1987 | Stempfle et al. |
| 5,055,203 | A * | 10/1991 | Columbus ............... 210/741 |
| 5,957,895 | A | 9/1999 | Sage et al. |
| 5,984,912 | A * | 11/1999 | Niedospial et al. ............ 604/408 |
| 6,485,461 | B1 | 11/2002 | Mason et al. |
| 6,485,471 | B1 * | 11/2002 | Zivitz et al. ............... 604/212 |
| 6,589,229 | B1 | 7/2003 | Connelly et al. |
| 6,723,072 | B2 | 4/2004 | Flaherty et al. |
| 6,740,059 | B2 | 5/2004 | Flaherty |
| 8,491,565 | B2 * | 7/2013 | Yodfat et al. ............... 604/500 |
| 2001/0010802 | A1 | 8/2001 | Tamari |
| 2002/0169439 | A1 | 11/2002 | Flaherty |
| 2003/0097092 | A1 | 5/2003 | Flaherty |
| 2004/0068224 | A1 | 4/2004 | Couvillon et al. |
| 2004/0116847 | A1 | 6/2004 | Wall |
| 2005/0277882 | A1 * | 12/2005 | Kriesel ............... 604/131 |
| 2006/0264829 | A1 | 11/2006 | Donaldson |
| 2007/0016159 | A1 | 1/2007 | Sparholt et al. |
| 2007/0066955 | A1 | 3/2007 | Sparholt et al. |
| 2007/0088271 | A1 * | 4/2007 | Richards ............... 604/151 |
| 2007/0106218 | A1 | 5/2007 | Yodfat et al. |
| 2008/0097318 | A1 * | 4/2008 | Adams ............... 604/131 |
| 2008/0215035 | A1 | 9/2008 | Yodfat et al. |
| 2010/0298764 | A1 | 11/2010 | Yodfat et al. |

FOREIGN PATENT DOCUMENTS

| | | |
|---|---|---|
| WO | WO-03089789 A2 | 10/2003 |
| WO | WO-2005082436 A1 | 9/2005 |
| WO | WO-2006108809 A1 | 10/2006 |

OTHER PUBLICATIONS

International Search Report & Written Opinion for PCT Application No. PCT/IL2008/000998, mailed Feb. 9, 2009.

Melbert et al., "Insulin Compatibility with Polymer Materials Used in External Pump Infusion Systems", *Diabetic Med.*, 5(3):243-247 (1988).

Tarr et al., "Stability and sterility of biosynthetic human insulin stored in plastic insulin syringes for 28 days", *Am. J. Hosp. Pharm.*, 48(13):2631-2634 (1991).

International Search Report for PCT Application No. PCT/IL2008/000998, mailed Feb. 9, 2009.

* cited by examiner

COLLAPSIBLE RESERVOIR FOR USE WITH A DELIVERY DEVICE

CROSS-REFERENCE TO RELATED APPLICATIONS

This application is a continuation of U.S. patent application Ser. No. 12/452,693, filed on Jan. 13, 2010, now U.S. Pat. No. 8,491,565, which is a 35 U.S.C. §371 national stage entry of PCT/IL2008/000998, which has an international filing date of Jul. 20, 2008 and claims priority to U.S. Provisional Patent Application Nos. 60/961,528, 60/961,484 and 60/961,382, all of which were filed in the U.S. Patent & Trademark Office on Jul. 20, 2007. The present application incorporates herein by reference the contents of each of the above-referenced applications in their entireties.

FIELD OF INVENTION

Embodiments of the present disclosure relate generally to a device and a method to deliver fluid (e.g., therapeutic fluid, such as insulin) into the body. In some embodiments, a portable device is provided that infuses a drug using a peristaltic mechanism. In some embodiments, a miniature skin-securable infusion device is provided that uses a collapsible reservoir.

BACKGROUND

Diabetes mellitus is a disease of major global importance, increasing in frequency at almost epidemic rates, such that the worldwide prevalence in 2006 is 170 million people and is predicted to at least double over the next 10-15 years. Diabetes is characterized by a chronically raised blood glucose concentration (hyperglycemia) due to a relative or absolute lack of the pancreatic hormone, insulin. Generally, normal pancreatic islet cells (beta cells) continuously sense the blood glucose levels and consequently regulate insulin secretion to maintain near constant glucose levels.

Diabetes mellitus patients require the administration of varying amounts of insulin throughout the day to control their blood glucose levels. In recent years, ambulatory portable insulin infusion pumps have emerged as a superior alternative to multiple daily injections of insulin. These pumps, which deliver insulin at a continuous basal rate as well as in bolus volumes, were developed to liberate patients from repeated self-administered injections, and allow greater flexibility in dose administration. Both basal and bolus volumes have to be delivered in precise doses, according to individual prescription, since an under or overdose of insulin could be fatal. Therefore, insulin injection pumps have to provide high reliability to prevent delivery of an unintentional insulin excess or shortage.

Several ambulatory insulin infusion devices are currently available on the market. The first generation of disposable syringe-type reservoirs and tubes are described, for example, in U.S. Pat. Nos. 2,631,847, 3,771,694, 4,657,486, and 4,544,369, the contents of which are hereby incorporated by reference in their entireties. Generally, the reservoirs of these devices are symmetrical, round, and tubular-shaped, and have rigid walls to enable smooth movement of the pump piston (plunger) and to maintain proper sealing.

Some of the drawbacks of these devices include their large size and weight, caused by the spatial configuration and the relatively large driving mechanism of the syringe and the piston. The relatively bulky devices have to be carried in a patient's pocket or be attached to the patient's belt. Consequently, the fluid delivery tube is long, usually longer than 60 cm, to enable needle insertion in remote sites of the body. These uncomfortable bulky fluid delivery devices with long tubing are not popular with the majority of diabetic insulin users, because these devices interfere with regular activities, such as sleeping and exercising (e.g., swimming). Furthermore, the effect of the image projected on a teenagers' body is unacceptable among teenagers. In addition, the use of a long delivery tube excludes some optional remote insertion sites, like the buttocks and the extremities.

To avoid tubing limitations, a second generation of pumps has been developed. These pumps include a housing having a bottom surface adapted for attachment to the user's skin, a reservoir disposed within the housing, and an injection needle adapted to be in fluid communication with the reservoir. These skin adhered devices typically are discarded of every 2-3 days, similarly to the infusion sets employed with the pumps of the first generation. Such second generation devices are described, for example, in U.S. Pat. Nos. 4,498,843, 5,957,895, 6,589,229, and 6,740,059, the contents of which are hereby incorporated by reference in their entireties. Other configurations of skin-secured pumps are disclosed, for example, in U.S. Pat. Nos. 6,723,072 and 6,485,461, the contents of which are hereby incorporated by reference in their entireties. The reservoirs of such devices, like the reservoirs used in 1st generation pumps, are usually tubular and syringe like, thus requiring a relatively large occupying space and a thick housing.

To address the volume and cost constraints, a 3rd generation skin-secured pump was proposed as described, for example, in commonly-owned patent applications PCT/IL06/001276 (Publication No. WO 2005/052277), entitled "Modular portable Infusion Pump" and U.S. patent application Ser. No. 11/397,115, entitled "Systems and methods for sustained medical infusion and devices related thereto", filed Apr. 3, 2006, the contents of which are hereby incorporated by reference in their entireties. Various embodiments of the device include some or all of the following components:

1—A dispensing patch unit—the dispensing patch unit includes two parts, a disposable part and a reusable part. The reusable part generally includes electronic components and the metering portion. The disposable part generally includes a reservoir for therapeutic fluid, a short delivery tube and an exit port. Buttons on the reusable part enable manual bolus delivery and/or specifying other commands and control operations. After connection of the reusable and disposable parts, the assembled device has a very thin dimension, rendering the whole device inexpensive, light and discrete.

2—A remote control unit for data acquisition, programming, and communication of user input.

3—A cradle unit—a skin securable piece with, for example, adhesive that is connected to the skin and enables connection and disconnection of the dispensing patch unit.

4—A cannula cartridge unit—a cannula and a penetrating member are shielded within a protecting case. The cartridge can be loaded into an automatic inserter that fires the cannula into the body through a cradle opening.

SUMMARY OF THE INVENTION

Described herein are fluid delivery devices and associated methods to deliver therapeutic fluid from a collapsible reservoir to a patient's body, where the collapsible nature of the reservoir enables, for example, more efficient use of the therapeutic fluid.

In some embodiments of the disclosure, a device and a method for storing a therapeutic liquid (e.g., insulin) for a period of time to be used in a fluid delivery, skin-adherable dispensing patch is provided. The device and method may employ a collapsible reservoir configured to house the therapeutic fluid, and to collapse in response to delivery of the fluid from the reservoir to a patient's body. In some embodiments, the dispensing patch may be remotely controlled and may be composed of two parts, a reusable part and a disposable, each part having its own housing. In some embodiments, an aperture for pressure equilibration with outside atmosphere may be provided. The reusable part may include, for example, a metering portion and electronics and the disposable part may include, for example, the reservoir, the delivery tube and an exit port. In some embodiments, in addition to the insulin delivery function of the device, the device may include one or more components/modules to perform, for example, continuous glucose monitoring. In some embodiments, the dispensing patch may be attached to the patient's skin with a cradle that enables connection and disconnection. In some embodiments, the dispensing patch may employ a peristaltic positive displacement pumping mechanism, which may include a rotary wheel that squeezes a delivery tube in order to positively displace fluid from the collapsible reservoir to the exit port.

In some embodiments, a transparent, collapsible, watertight reservoir may be provided that includes a multi-layered film formed into a geometrically uniquely shaped pouch or shell (e.g., a shape substantially matching the shape of a cavity of a fluid delivery device). In some embodiments, the reservoir may include a pliable shell defining a varying inner volume that varies based on the volume of therapeutic fluid held inside the reservoir, the varying inner volume having a predetermined maximum volume for containing a corresponding volume of therapeutic fluid. The pliable shell includes an outlet port for communicating fluid from the reservoir to a patient, the varying inner volume decreasing upon therapeutic fluid being communicated through the exit port. Upon the reservoir reaching the predetermined maximum volume when being filled with therapeutic fluid, any therapeutic fluid in excess of the predetermined maximum volume driven into the reservoir causes a substantially corresponding amount of therapeutic fluid to exit out of the reservoir via the outlet port and/or at least one other port provided in the pliable shell. The shell may be constructed from a multi-layered material that includes, for example, a three-layered material that includes an inner layer, a middle layer and an outer layer. The inner layer of the reservoir may be made from a material with a low temperature melting point, thus enabling heat welding. An outer layer of the material of the reservoir may resist high temperature(s) including welding temperature(s). The reservoir may be sufficiently moisture proof, preservative (e.g. phenol, m-cresol) proof and/or $CO_2$ proof to enable for storage of a medicament containing water and preservatives (e.g., phenol, m-cresol), without significant changes in potency of medicament for the entire usage duration (e.g., 3-4 days). The reservoir's geometrical structure may enable for optimal filling of the fluid and complete or almost complete emptying with minimal if any residual volume. The shell (pouch) may have a self-sealable inlet port that is made of, for example, rubbery material (e.g., silicone) and an exit port that includes a short rigid tube for connecting the delivery tube. During filling, fluid may enter the reservoir and entrapped air may leave the reservoir through the exit port, and the unique configuration of the reservoir may avoid spilling of fluid into the delivery tube before filling completion (full tank) and trapping of air bubbles during operation.

In some embodiments, methods for forming a collapsible reservoir are also disclosed. For example, reservoir polymer films may be shaped by vacuum forming and then welded together with the inlet and outlet port assemblies without gluing.

In some embodiments, the collapsible reservoir may be provided for use in connection with a dispensing mechanism included within the 3rd generation skin securable devices described above. The dispensing mechanism may utilize, for example, peristaltic positive displacement. In some embodiments, a drug (e.g., insulin) is stored in the reservoir. The reservoir itself may be disposed in a reusable part of the device. A resilient tube (hereinafter the "delivery tube") may emerge from the reservoir and maintain fluid communication between the reservoir and an exit port. The peristaltic mechanism may positively displace fluid from the reservoir by periodically applying suction forces on the delivery tube. In some embodiments, the reservoir may have one or more (e.g., all) of the following mechanical and chemical characteristics:

Collapsible—the peristaltic pumping mechanism may force fluid movement within the delivery tube in the direction of rotation and consequently suction of fluid from the reservoir. As a result, the volume of fluid within the reservoir may decrease and, if no air gets inside, the reservoir walls collapse.

Maximal filling capacity and minimal residual volume—the reservoir may be compliant (expandable) during filling and emptied to minimal residual volume.

Resistance to inward and outward pressure that can be induced by over filling and unintentional external impact, respectively.

Inclusion of a filling port that enables reservoir puncturing and an exit port in communication with the delivery tube.

In some embodiments of the present disclosure, a portable medical device for sustained infusion of therapeutic liquids into the body is provided. The device may be thin, have a small footprint, with no external tubing, and may be secured (e.g., adhered) to a patient skin (e.g., skin adherable dispensing patch).

In some embodiments, a skin securable patch is provided that includes two parts: a reusable part and a disposable part. The reusable part may contain the relatively expensive components (e.g., electronics, etc.) while the disposable part may contain the relatively inexpensive components, as well the components that generally have to be provided to a patient in sterile condition (e.g., needles) and the reservoir.

In some embodiments, a two-part skin-adherable dispensing patch is provided that employs a peristaltic pumping mechanism. The pump components may be divided between the reusable and disposable parts. Such pump components may include the metering portion (including a rotary wheel) which is contained within the reusable part, and the sterile delivery tube which is contained within the disposable part. Squeezing of the delivery tube by the rotary wheel positively displaces liquid from the reservoir which causes the reservoir's walls to collapse to avoid entry of air into the therapeutic fluid.

In some embodiments, a two-part skin-adherable dispensing patch is provided, with each part having a separate housing and an aperture. The aperture in the housing(s) enables air entry into the patch to thus achieve pressure equilibrium with the surrounding atmosphere. The aperture may be sealed by a waterproof member. Pressure equilibration enables the reservoir to collapse during emptying and during altitude change (e.g., in flight).

In some embodiments of the present disclosure, a collapsible reservoir for storing a therapeutic liquid solution (e.g., insulin), where the reservoir can collapse during liquid delivery into a user's body, is provided. In some embodiments, the collapsible reservoir is contained in a disposable part of the dispensing patch.

In some embodiments, a reservoir is provided that has mechanical characteristics that make it suitable for collapse and can be made of one or more polymeric layers.

In some embodiments, a collapsible reservoir is provided that is spatially economical in that it conforms to a patch housing to thus enable the skin-securable patch to remain thin with a small footprint.

In some embodiments, a collapsible reservoir that avoids trapping of air bubbles is disclosed.

In some embodiments of the present disclosure, a collapsible reservoir that is biocompatible is provided.

In some embodiments, a collapsible reservoir is provided that holds fluids and maintains the chemical stability of a drug and/or preservatives held in the reservoir, and also avoids leachable material.

In some embodiments, a collapsible reservoir is provided that enables concomitant filling of therapeutic fluid and exit of air.

In some embodiments, a collapsible reservoir is provided that enables complete filling (full capacity) before fluid spills from the outlet port.

In some embodiments of the present disclosure, a collapsible reservoir that can collapse to a minimal size with minimal if any residual volume of fluid is provided.

In some embodiments, a collapsible reservoir is provided that is constructed from materials that prevent evaporation (water and antibacterial preservative) and also prevents the diffusion of, for example, $CO_2$ from the surroundings into the reservoir.

In some embodiments, a collapsible reservoir is provided that has an inlet port that enables filling and maintains sealing and can be filled by a syringe or by a designated adapter.

In some embodiments, a collapsible reservoir is provided that has an outlet port that is connected to the delivery fluid in a way that prevents entrapment of air bubbles.

In some embodiments of the present disclosure, a collapsible reservoir that can be sterilized, for example, by ETO (ethylene oxide) is provided.

In some embodiments, a collapsible reservoir is provided that can be manufactured by a production method (e.g., vacuum forming and/or welding) that maintains its biocompatibility and that avoids use of adhesive materials such as glue. The reservoir may be welded and the inlet and outlet ports may be connected by pressure.

In some embodiments, a collapsible reservoir is provided that is composed of inexpensive materials, is easy to assemble, and has a relatively low production cost.

In one aspect, a therapeutic fluid reservoir to be used with an ambulatory portable infusion device is disclosed. The reservoir includes a pliable shell defining a varying inner volume that varies based on the volume of therapeutic fluid held inside the reservoir, the varying inner volume having a predetermined maximum volume for containing a corresponding volume of therapeutic fluid and an outlet port for communicating fluid from the reservoir to a patient, the varying inner volume decreasing upon therapeutic fluid being communicated through the outlet port. Upon the reservoir reaching the predetermined maximum volume when being filled with therapeutic fluid, any therapeutic fluid in excess of the predetermined maximum volume driven into the reservoir causes a substantially corresponding amount of therapeutic fluid to exit out of the reservoir via the outlet port and/or at least one other port provided in the pliable shell.

Embodiments of the reservoir may include one or more of the following features.

The shell may be configured to collapse from a first volume to a second, smaller, volume, as the fluid is removed from the varying inner volume defined by the shell. The second smaller volume may be limited by a minimum volume that can be reached by the pliable shell as the fluid is removed from the varying inner volume.

The shell may include at least two portions including a first portion coupled to a second portion. The first portion may be coupled to the second portion such that the first portion is welded to the second portion.

The at least one other port may include at least one filling port to receive the fluid to fill the inner volume. The at least one filling port may include an inlet pipe and a self sealable septum connectable to the inlet pipe.

The reservoir may further include a delivery tube connectable to the outlet port to direct the fluid removed through the outlet port to the patient. The reservoir may further include an adapter to connect the delivery tube to the outlet port, the adapter configured to receive at least a section of the delivery tube pressured to the adapter.

The pliable shell may include a transparent portion through which the therapeutic fluid held within the reservoir is visible.

The outlet port may be received within an opening defined in the pliable shell. The opening defined in the pliable shell may be located in a narrow portion of the shell.

The reservoir may further include a connector to couple the outlet port to the pliable shell, the connector secured in an opening defined in the pliable shell.

The shell may be constructed from a material configured to substantially resist further outward expansion when the inner volume is at its maximum volume, and to contract inwardly when the fluid exits the inner volume.

The shell may be constructed from a multi-layered material. The multi-layered material may include an inner low temperature resistant polymer layer, a middle thermoplastic elastomer (TPE) layer coupled to the inner layer, and an outer high temperature resistant polymer layer coupled the middle layer.

The inner polymer layer may include one or more of, for example, polypropylene, polyethylene and/or propylene-ethylene copolymer.

The outer polymer layer may include one or more of, for example, polypropylene, polytetrafluoroethylene (PTFE), polyvinylidenechloride (PVDC) and/or ethylene vinyl alcohol copolymer (EVOH).

The multi-layered material may further include one or more adhesive layer to couple any two of the inner layer, the middle layer and the outer layer.

The inner layer may have a thickness of about 1-25 μm, the middle layer may have a thickness of about 2-40 μm and the outer layer may have a thickness of about 3-15 μm The shell may be constructed from a material having a thickness less than 100 μm The shell may be constructed from a material comprising a single polymer layer comprising one or more of, for example, polypropylene, polyethylene and/or propylene-ethylene copolymer.

The shell may be constructed from a material configured to be resistant to ethylene oxide (ETO) sterilization such that characteristics of the material do not degrade during application of ETO sterilization procedure to the shell.

The shell may be constructed from a material configured to be resistant to sterilization procedures including one or more of gamma irradiation procedure and steam sterilization procedure, such that characteristics of the material do not degrade during application of the sterilization procedures to the shell.

The therapeutic fluid may include insulin.

The varying inner volume may include rounded corners such that trapping of gases and/or liquids within the varying inner volume is reduced. The rounded corners of the varying inner volume may have respective radii of curvature of between 1 and 1.4 mm.

The shell may have an irregular, amorphous shape such that the shell is adapted to fit within any housing having a volume at least equal to a volume occupied by the shell when the varying inner volume is at the maximum volume.

The maximum volume of the varying inner volume may be at most 3 ml.

In another aspect, an ambulatory portable dispensing device to deliver a therapeutic fluid to a patient's body is disclosed. The dispensing device includes a reservoir to hold the therapeutic fluid, wherein the reservoir is configured to collapse from a first volume to a second, smaller volume as the therapeutic fluid is removed from the reservoir, and a pump configured to cause the delivery of the therapeutic fluid from the reservoir to the patient's body.

Embodiments of the device may include any of the features of the reservoir, as well as any one of the following features.

The reservoir may include a pliable shell defining a varying inner volume that varies based on the volume of the therapeutic fluid held inside the reservoir, the varying inner volume having a predetermined maximum volume for containing a corresponding volume of therapeutic fluid and an outlet port for communicating fluid from the reservoir to a patient, the varying inner volume decreasing upon therapeutic fluid being communicated through the outlet port. Upon the reservoir reaching the predetermined maximum volume when being filled with therapeutic fluid, any therapeutic fluid in excess of the predetermined maximum volume driven into the reservoir may cause a substantially corresponding amount of therapeutic fluid to exit out of the reservoir via the outlet port and/or at least one other port provided in the pliable shell.

The device may further include a delivery tube connectable to the outlet port to direct the therapeutic fluid removed through the outlet port to a unit configured to dispense the directed therapeutic fluid.

The device may further include the unit configured to dispense the directed therapeutic fluid.

The unit configured to dispense the directed therapeutic fluid may include a needle unit to detachably secure the unit to the patient's body. The needle unit may be associated with the subcutaneously delivery of the therapeutic fluid received from the reservoir to the patient's body.

The reservoir may be configured to hold insulin.

The pump may be a peristaltic pump.

The device may further include a dispensing patch to house the reservoir and the pump, the dispensing patch configured to be securable to the patient's body.

The dispensing patch may include a reusable part including the pump, and a disposable part having the reservoir and the outlet port.

The device may further include a venting mechanism to cause air pressure equilibration within the dispensing patch, the venting mechanism disposed at the dispensing patch.

The venting mechanism may include one or more of, for example, an aperture and/or a membrane with selective permeability to enable entry of air into the dispensing patch and prevent entry of aqueous solutions.

The device may further include a remote control unit to communicate data regarding operation of the dispensing device.

In a further aspect, a method for constructing a collapsible reservoir to hold therapeutic fluid for use with an ambulatory portable infusion device is disclosed. The method includes coupling at least two portions including a first portion and a second portion of a pliable shell to define a varying inner volume that varies based on the volume of therapeutic fluid held inside the reservoir, the varying inner volume having a predetermined maximum volume for containing a corresponding volume of the therapeutic fluid. The pliable shell includes an outlet port for communicating fluid from the reservoir to a patient, the varying inner volume decreasing upon therapeutic fluid being communicated through the outlet port. Upon the reservoir reaching the predetermined maximum volume when being filled with the therapeutic fluid, any therapeutic fluid in excess of the predetermined maximum volume driven into the reservoir causes a substantially corresponding amount of therapeutic fluid to exit out of the reservoir via the outlet port and/or at least one other port provided in the pliable shell.

Embodiments of the method may include any of the features described in relation to the reservoir and/or device, as well as any one of the following features.

Coupling the first portion to the second portion of the shell may include coupling the first portion to the second portion of a shell made from a material configured to substantially resist outward expansion when the inner volume is at its maximum volume, and to contract inwardly when the fluid exits the inner volume.

Coupling the first portion to the second portion of the shell may include welding the first portion to the second portion of the shell.

The method may further include forming the outlet port and the at least one other port. Forming the outlet port and the at least one other port may include placing an inlet pipe and an outlet pipe between the first portion and the second portion of the shell.

The method may further include placing an adapter into the outlet pipe, the adapter configured to receive a delivery tube to direct the therapeutic fluid removed through the outlet port.

At least one of the inlet pipe and the outlet pipe may be received in an opening in the reservoir, the at least one of the inlet pipe and the outlet pipe is retained by pressure rendered by the coupling of the first portion to the second portion of the shell.

The opening defined in the shell may be located in a narrow portion of the shell.

Coupling the first portion and the second portion of shell may include coupling the first and second portion of a shell made from a multi-layered material.

Coupling the first portion and the second portion of shell may include coupling the first and second portion of a shell made from a material having a thickness less than 100 gm.

Coupling the first portion and the second portion of the shell may include coupling the first and second portion of a shell made from a single polymer layer comprising one or more of, for example, polypropylene, polyethylene and/or propylene-ethylene copolymer.

Coupling the first portion and the second portion of the shell may include coupling the first and second portion of a shell made from a material configured to be resistant to ethylene oxide (ETO) sterilization such that characteristics of the material do not degrade during application of ETO sterilization procedure to the shell.

Coupling the first portion and the second portion of the shell may include coupling the first and second portion of a shell made from a material configured to be resistant to sterilization procedures including one or more of gamma irradiation procedure and steam sterilization procedure, such that characteristics of the material do not degrade during application of the sterilization procedures to the shell.

Coupling the first portion and the second portion of the shell may include heating a section of a material used to make the shell, and placing the heated section of the material into a first and second pre-made molds, the first and second molds having respective shapes corresponding to the first portion and the second portion of the shell.

Placing the heated section of the material into the first and second pre-made molds may include creating a vacuum to direct the heated material to be placed into the first and second pre-made molds.

The method may further include cooling the material placed in the first and second pre-made molds, and removing the cooled materials to obtain the first and second portions of the shell.

BRIEF DESCRIPTION OF THE DRAWINGS

Embodiments of the present disclosure, including the various objects and advantages thereof, are described in reference to the following illustrative drawings.

DRAWINGS AND DETAILED DESCRIPTION OF INVENTION

Figure 1A:
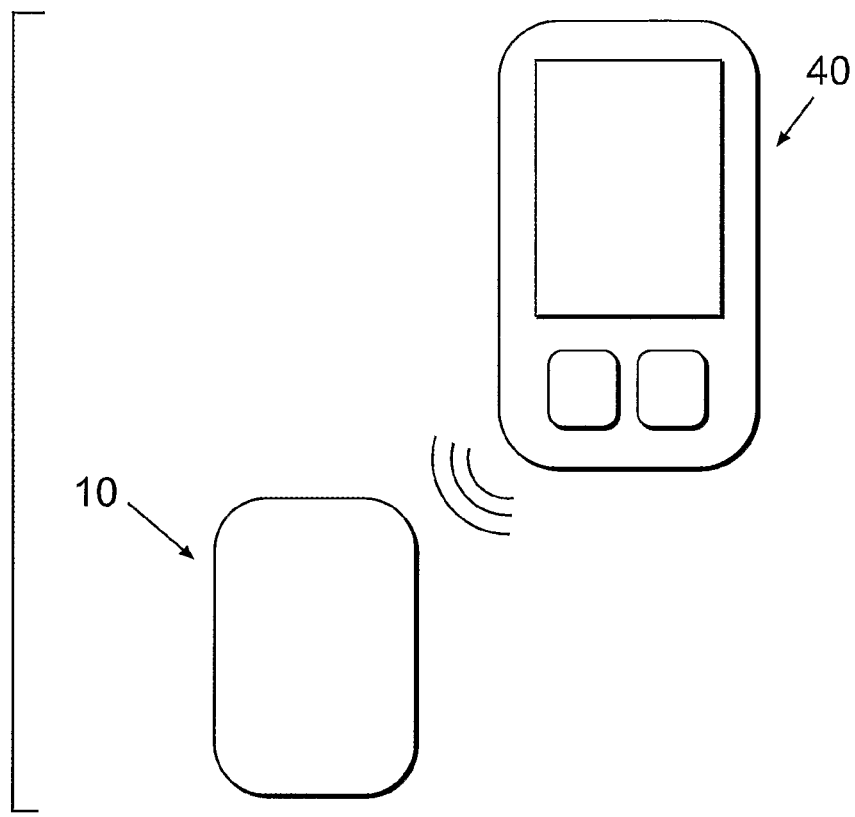
FIGS. 1a, 1b and 1c are schematic diagrams of exemplary embodiments of fluid delivery devices.

Generally, as used herein a "collapsible" item refers to an item that caves inwardly with relative ease, and which generally does not break, tear or otherwise compromise its structural integrity due to the collapsing. A collapsible reservoir caves inwardly as the fluid contained within the reservoir empties from the reservoir during, for example, the performance of fluid delivery operations. A collapsible reservoir may thus collapse gradually without breaking. As used herein "PP" designates polypropylene; "TPE" designates thermo plastic elastomer; and "IU" designates insulin units.

Disclosed herein is a collapsible reservoir to hold therapeutic fluid, such as insulin, for use with an ambulatory portable infusion device. The reservoir includes a pliable shell defining a varying inner volume that varies based on the volume of therapeutic fluid held inside the reservoir, the varying inner volume having a predetermined maximum volume for containing a corresponding volume of therapeutic fluid. The pliable shell also includes an outlet port for communicating fluid from the reservoir to a patient, the varying inner volume decreasing upon therapeutic fluid being communicated through the outlet port. Upon the reservoir reaching the predetermined maximum volume when being filled with therapeutic fluid, any therapeutic fluid in excess of the predetermined maximum volume driven into the reservoir causes a substantially corresponding amount of therapeutic fluid to exit out of the reservoir via the outlet port and/or at least one other port provided in the pliable shell. Also disclosed is a dispensing device to deliver a therapeutic fluid to a patient's body that includes a collapsible reservoir to house the therapeutic fluid, the reservoir configured to collapse from a first volume to a second, smaller volume as the therapeutic fluid is removed from the reservoir. In some embodiments, the dispensing device includes a pump to cause the delivery of the therapeutic fluid from the reservoir to the patient's body. In some embodiments, the second smaller volume may be limited by a minimum volume that may be reached by the shell as fluid is removed from the inner volume of the reservoir (shell).

As will become apparent below, the material from which the shell constituting the collapsible reservoir is constructed, and the material structural properties (e.g., thickness, hardness, and elongation) are such that it does not extend when filled. The material is rigid, but the wall is generally very thin, and thus the reservoir volume can be changed only when there is a force/pressure on the reservoir's walls. When the reservoir is being filled the outlet port is small enough to enable pressure build-up by the fluid to expend the reservoir to its maximal volume, and upon reaching the max volume fluid flows through the outlet port. When pumping, i.e. emptying the reservoir, the inlet port of the shell (reservoir) is sealed by a septum, and thus the removal of the fluid creates a vacuum inside the reservoir causing the shell's walls to collapse inwardly.

Figure 1B:
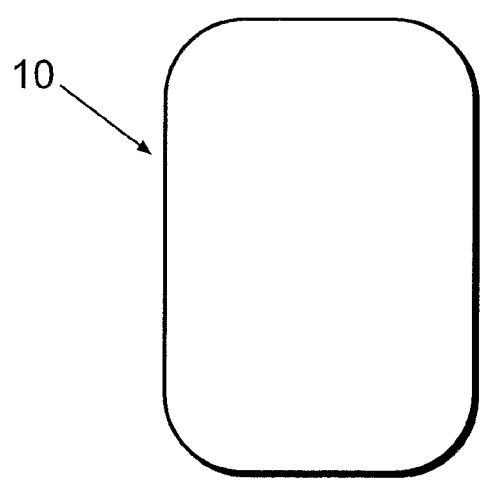
Figure 1C:
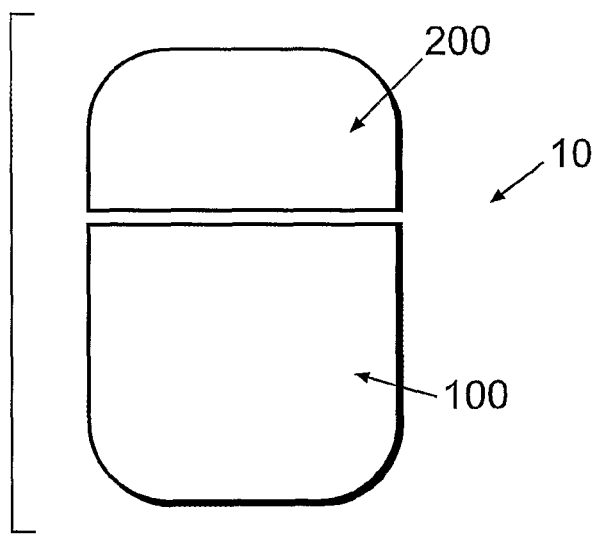

Referring to FIGS. 1a, 1b and 1c, schematic diagrams of exemplary fluid delivery devices are shown. As more particularly shown in FIG. 1a, the fluid delivery device includes a dispensing unit 10 and a remote control unit 40. In some embodiments of the present disclosure, the dispensing unit 10 may be a single part (as more particularly shown in FIG. 1b) or it may be a two part unit, as shown, for example, in FIG. 1c, that includes a reusable part 100 and a disposable part 200.

The dispensing unit 10 may employ different dispensing mechanisms, such as, for example, a syringe-type reservoir with a propelling plunger, peristaltic positive displacement pumps, etc. Illustrative examples of fluid reservoirs are described in the context of mechanisms based on the use of a peristaltic positive displacement pumps. However, the fluid reservoirs described herein may be used with other types of dispensing mechanisms.

Figure 2A:
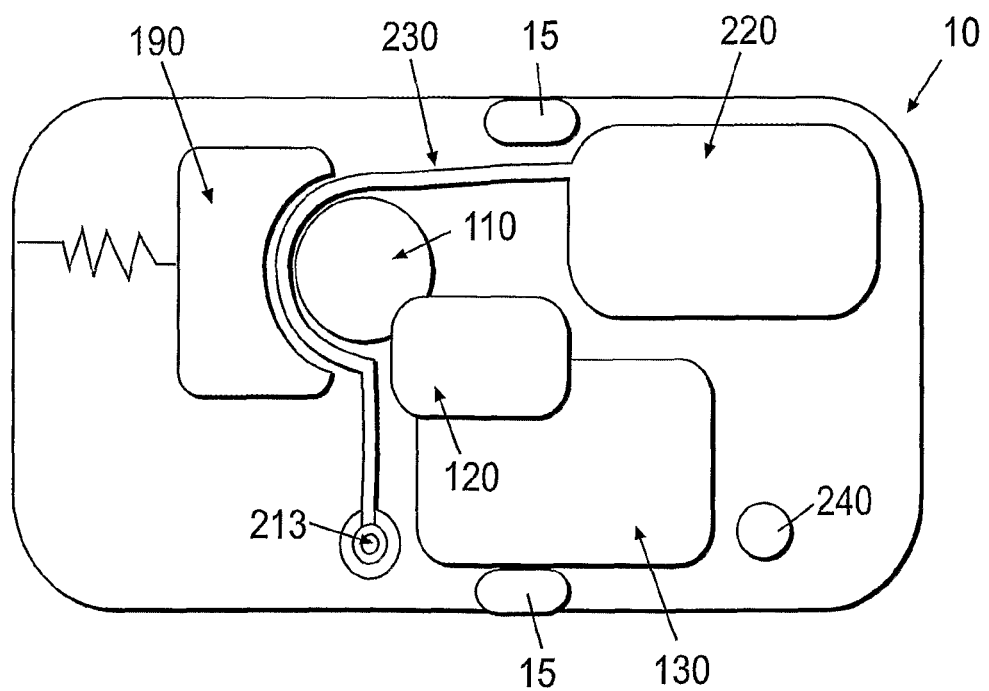
FIGS. 2a and 2b are schematic diagrams of exemplary embodiments of a single-part dispensing unit and a two-part dispensing unit, respectively.

Referring to FIG. 2a, a schematic diagram of an exemplary embodiment of a single-part dispensing unit 10 is shown. The single-part dispensing unit 10 is configured as a single housing in which a peristaltic mechanism (metering portion) is employed for dispensing fluid to a user's body. The fluid is delivered from a reservoir 220 through a delivery tube 230 to an outlet port 213. The peristaltic mechanism comprises a rotary wheel 110, rollers (not shown) and a stator 190. Rotation of the wheel and pressing of the rollers against the stator 190 periodically positively displaces fluid within the delivery tube 230 by virtue of a peristaltic motion. An example of a suitable positive displacement pump is disclosed in co-pending/co-owned U.S. patent application Ser. No. 11/397,115, entitled "Systems and methods for sustained medical infusion and devices related thereto" and filed Apr. 3, 2006, and International Patent Application No. PCT/IL06/001276 (PCT Publication No. WO 2005/052277, entitled "Modular portable Infusion Pump"), the contents of which are hereby incorporated by reference in their entireties. A driving mechanism 120, e.g., a stepper motor, a DC motor, a SMA actuator or the like, rotates the rotary wheel 110, and is controlled by a an electronic control module, schematically designated by reference numeral 130. The controller module 130 may be implemented using, for example, a processor-based device, a transceiver and/or other electronic components required to implement the control module The electronic of the electronic control module 130 may be arranged on a Printed Circuit Board (PCB), although a PCB is only an example of suitable implementation to arrange the electronic components constituting the control module and is not intended to be limiting. As further shown in FIG. 2a, the dispensing unit also includes an energy supply 240, which, in some embodiments, may include one or more batteries. Infusion programming can be performed by a remote control unit configured to establish a bidirectional communication link with the transceiver provided in the dispensing unit 10 and/or by manual buttons 15 disposed on the dispensing unit 10.

Figure 2B:
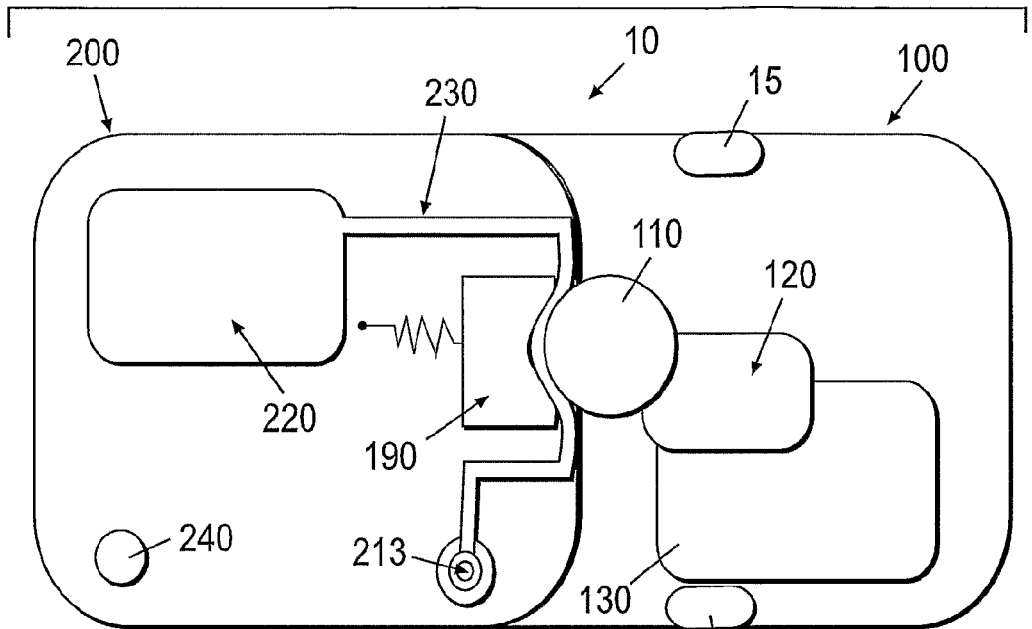

Referring to FIG. 2b, a schematic diagram of an exemplary two-part dispensing unit 10 is shown. The dispensing unit 10 includes a reusable part 100 and a disposable part 200, where each part is contained in a separate housing. The reusable part 100 includes the metering portion, for example, a positive displacement pump provided with a rotary wheel 110, a driving mechanism 120, a PCB 130 (e.g., including a control module implementation), and one or more manual buttons 15. The disposable part 200 may include a reservoir 220, a delivery tube 230, an energy supply 240, an outlet port 213 and a stator 190. Fluid dispensing can be enabled after connecting the reusable part 100 with the disposable part 200. An arrangement such as the one described herein is described, for example, in co-pending/co-owned U.S. patent application Ser. No. 11/397,115 and International Patent Application No. PCT/IL06/001276, the contents of which are hereby incorporated by reference in their entireties. A rotation monitoring module may also be provided (not shown) and may be included in either of the two parts of the dispensing unit 10. Energy supply 240, such as, for example, a battery, a fuel cell, a photovoltaic cell, or the like, may also be included in the disposable part 200 as shown. Alternatively, the energy supply 240 may be included in the reusable part 100.

Figure 2C:
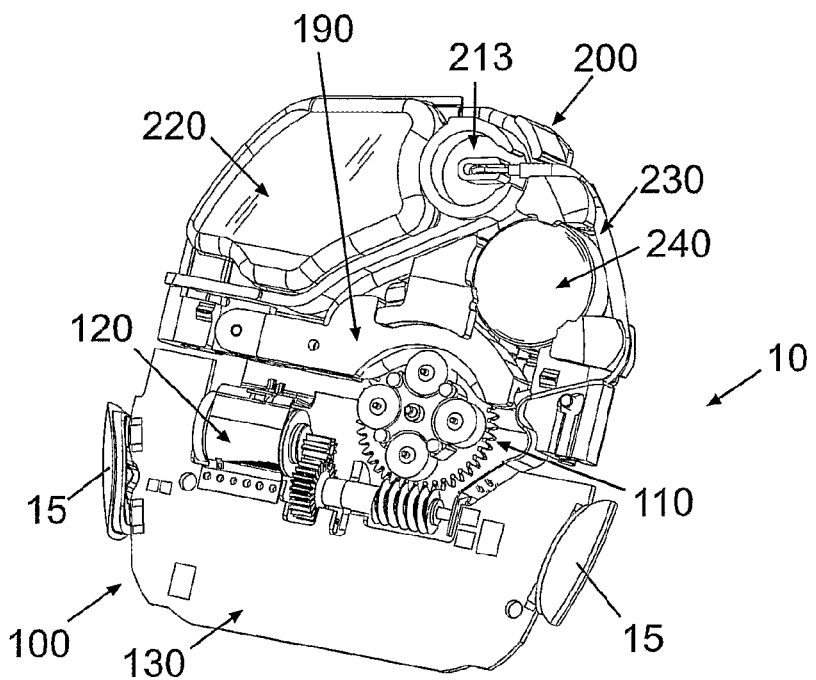
FIG. 2c is a view of an exemplary two-part dispensing unit.

Referring to FIG. 2c, a view of an exemplary embodiment of the two-part dispensing unit 10, with the reusable part (100) and the disposable part 200 connected, is shown. The reusable part 100 includes a positive displacement pump provided with a rotary wheel 110, a driving mechanism 120, a PCB 130, and manual button(s) 15. The disposable part 200 includes, in some embodiments, a reservoir 220 to hold the therapeutic fluid (e.g., insulin) that is to be dispensed, a delivery tube 230, energy supply 240, an outlet port 213 and a stator 190. In some embodiments, the pumping mechanism can be syringe-based mechanism, a mechanism implemented with piezoelectric-based devices, or the like.

Figure 3:
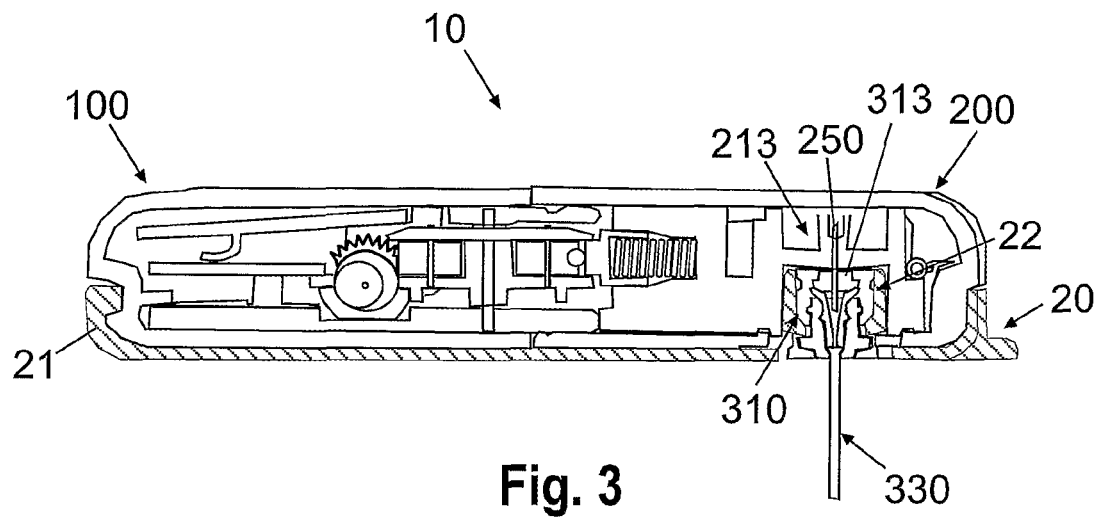
FIG. 3 is a schematic diagram of an exemplary fluid delivery device that includes a dispensing unit and a needle unit to connect the dispensing unit to the user's skin.

Referring to FIG. 3, a schematic diagram of an exemplary embodiment of a fluid delivery system (or device) that includes a dispensing unit 10, a remote control unit (not shown) and a needle unit 20, where the needle unit 20 (the needle unit is also referred to as the cradle unit and/or the cannula cartridge unit) is used to link the dispensing unit 10 to the user's skin and enable subcutaneous delivery of therapeutic fluid to the user's body. An exemplary needle unit, which may be similar to the needle unit 20 described herein, is disclosed in detail in, for example, commonly-owned patent application U.S. Ser. No. 12/004,837, filed Dec. 20, 2007, entitled "Systems, devices and methods for sustained delivery of a therapeutic fluid", the content of which is hereby incorporated by reference in its entirety. In some embodiments, the needle unit 20 comprises two parts: a cradle part 21 and a penetrating cartridge part 22, which includes a well portion 310, a cannula 330, a self-sealable septum 313, and a penetrating member. The cradle part 21 is secured to the user's skin by such mechanisms as, for example, adhesives. The penetrating member (not shown) is configured to prick the skin, leading the cannula (330) into the body, and thereafter being removed from the penetrating cartridge part 22, leaving the cannula 330 in the body.

The self-sealable septum 313 is positioned above the well 310, within the penetrating cartridge part 22, and enables repeated connection/disconnection with a connecting lumen 250 located at the end of the delivery tube 230 in the outlet port 213, within the dispensing unit 10. The self-sealable septum 313 also prevents leaking and entering of contamination. When the dispensing unit 10 is brought in close proximity with the needle unit 20, the connecting lumen 250 pierces the septum 313, enabling fluid communication between the cannula 330 and the reservoir (not shown in FIG. 3) via the delivery tube (not shown). As further shown in FIG. 3, the dispensing unit 10 is attached to the needle unit 20.

Figure 4A:
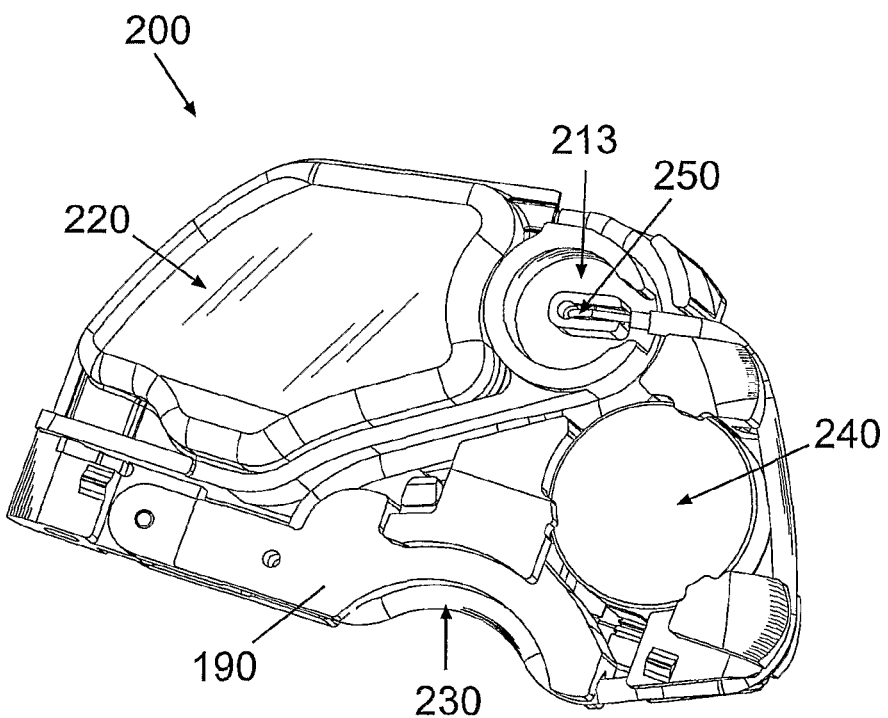
FIGS. 4a and 4b are an upper side view and a lower side view, respectively, of an exemplary disposable part of a dispensing unit and its components.
Figure 4B:
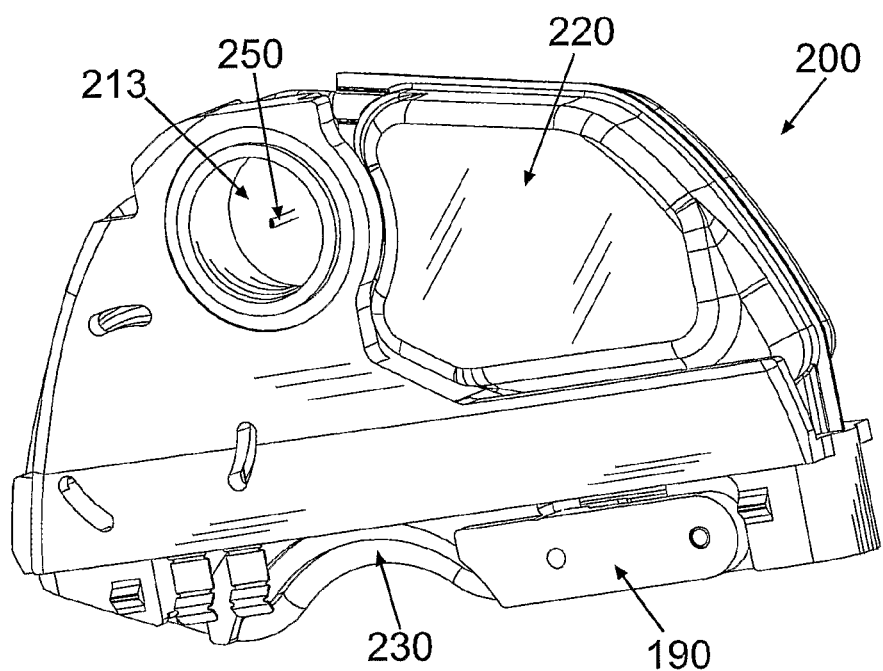

Referring to FIGS. 4a-b, upper and lower side views of an exemplary disposable part 200 is shown. The disposable part 200 includes a reservoir 220, a delivery tube 230, an energy supply 240, an outlet port 213, a connecting lumen 250, and a stator 190. In some embodiments, fluid within the reservoir 220 is displaced by the peristaltic movement in the delivery tube 230. The displaced fluid flows through the delivery tube 230 and through the connecting lumen 250 within the outlet port 213, into the cannula (not shown in FIGS. 4a and 4b) and into the body. In some embodiments, the reservoir 220 is a collapsible reservoir that collapses while emptying, to compensate for the displaced fluid and to avoid entry of air. In some embodiments, the reservoir can be made of a thin (e.g., smaller than 150 micron) non resilient polymer (e.g. polypropylene, polyethylene) that cannot be expanded during filling and can be collapsed during emptying.

Figure 5B:
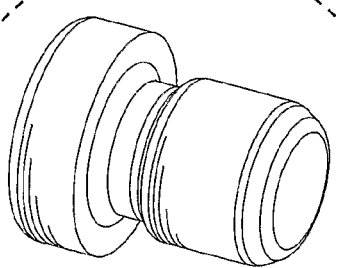
FIGS. 5a, 5b, 5c, 5d and 5e are views of exemplary components of a collapsible reservoir.
Figure 5A:
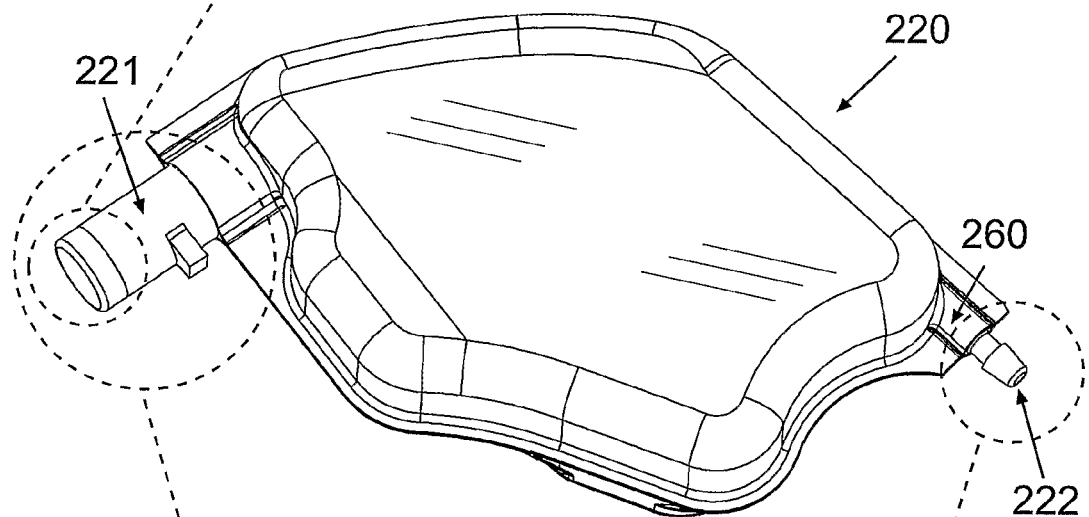
Figure 5C:
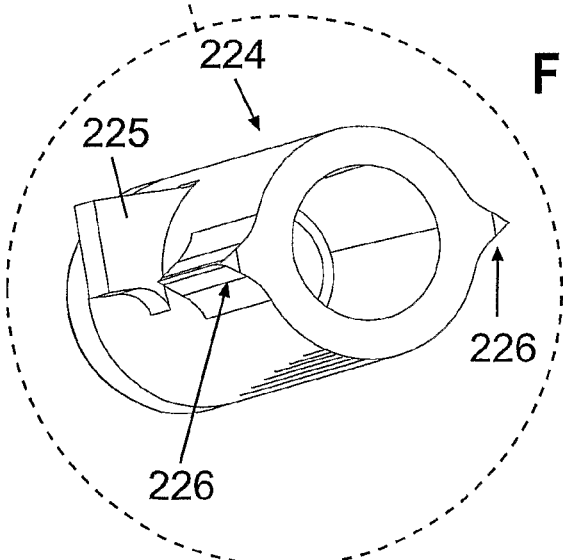
Figure 5D:
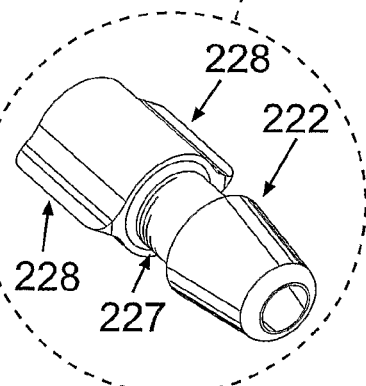

Referring to FIG. 5a, views of an exemplary embodiment of the collapsible reservoir 220 are shown. The collapsible reservoir 220 comprises an outlet port 260 and a filling port 221. The filling port 221 is located at one end of the reservoir 220, and enables filling and priming the collapsible reservoir 220 with a syringe needle not shown or by a complementary adapter (not shown). The filling port 221, shown in greater detail in FIG. 5c, comprises an inlet pipe 224 and a self-sealable septum 223 that is connectable to the inlet pipe 224, as shown in FIGS. 5a and 5b. The self-sealable septum 223 can be constructed of any rubbery material such as silicone, chlorobutyl, etc., and enables needle puncturing during filling to avoid leakage of water and entry of air. The septum has a general shape of a cylinder with one base, resembling a round glass, the needle goes through the base which is the self-sealable septum and into the cylinder.

The sealing of the reservoir 220 with the self-sealable septum 223 maintains the reservoir water-tight. The inlet pipe 224 contains a key tab 225, which is a protrusion that enables accurate positioning of the reservoir 220 within the disposable part (not shown) of the dispensing unit. Additionally, the inlet pipe 224 comprises two fins 226 for maintaining the reservoir 220 water-tight during the welding process, as will be described in greater details below.

As further shown in FIG. 5a, an adapter 222 is located on the reservoir outlet port 260. A delivery tube (an example of which is shown in FIG. 5b) is connected to the reservoir outlet port 260 via the adapter 222. In some embodiments, the adapter 222 includes two fins 228 to maintain the reservoir 220 water-tight during the welding process, as will be described in greater details below. The delivery tube is pressurized onto the adapter 222, and is held in place by means of an indentation groove (227).

Figure 5E:
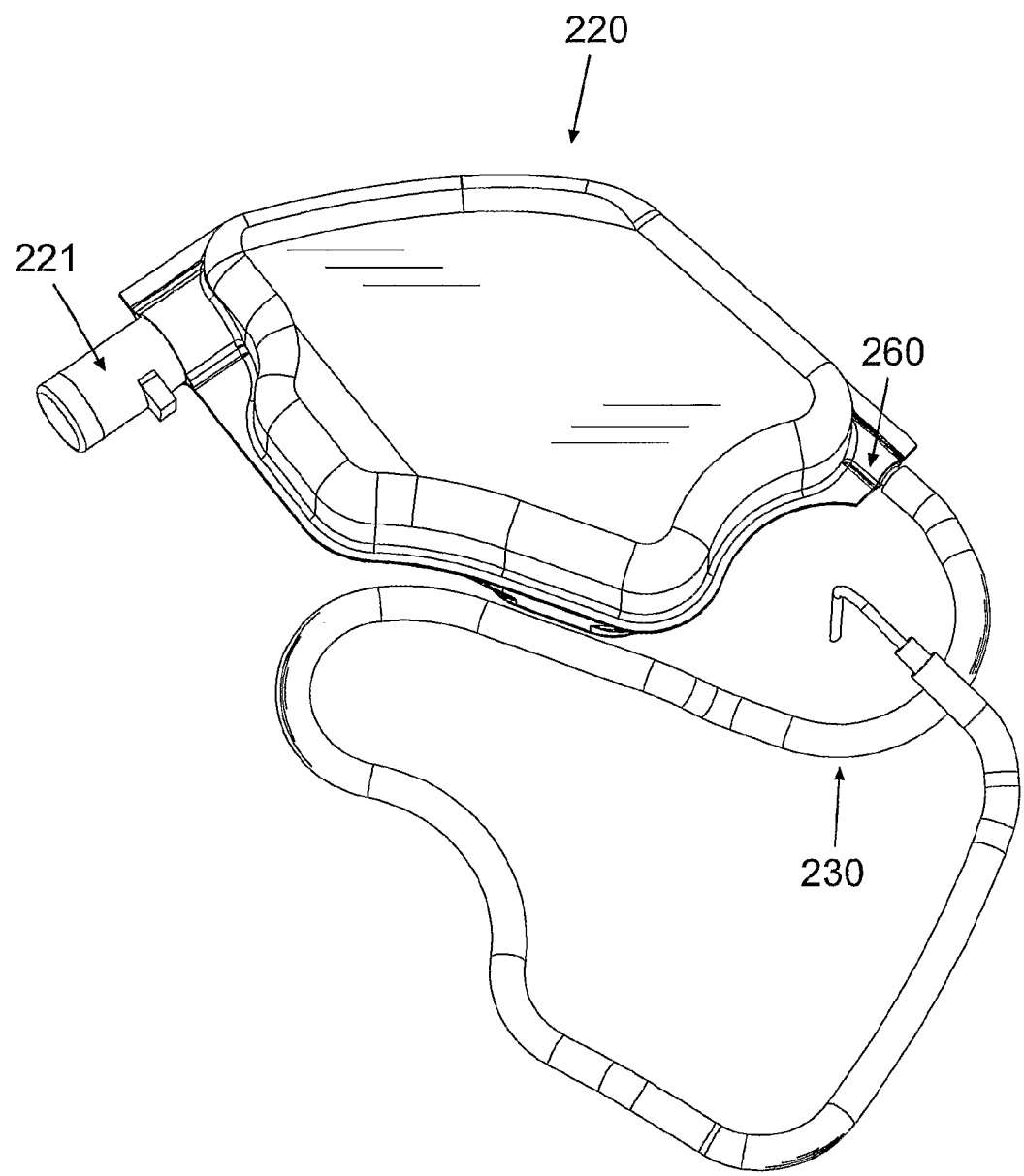

Referring to FIG. 5e, another exemplary embodiment of the collapsible reservoir 220 is shown. Like the collapsible reservoir depicted in FIG. 5a, the collapsible reservoir depicted in FIG. 5e includes a filling port 221. The collapsible reservoir shown in FIG. 5e does not have a connector secured to the outlet port 260. Rather, the delivery tube 230 is directly connectable to the reservoir outlet port 260.

Figure 6A:
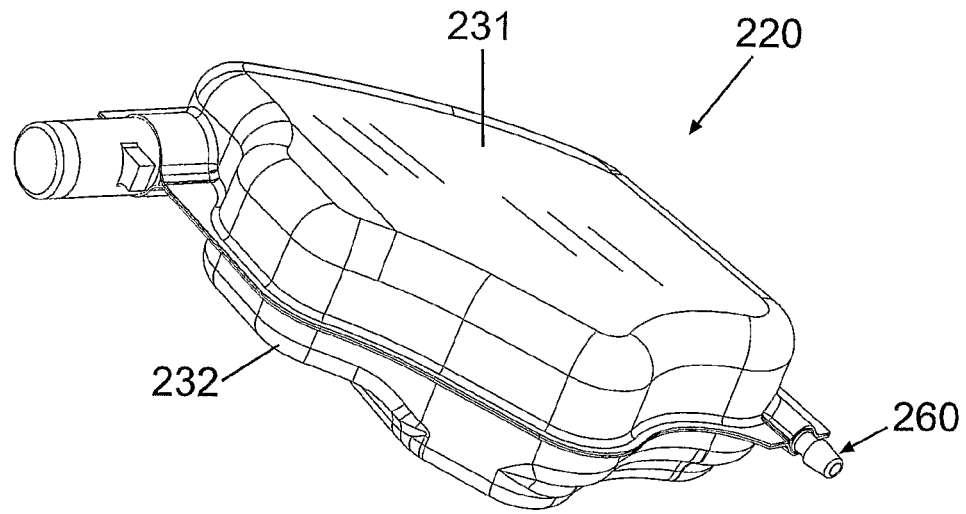
FIGS. 6a, 6b and 6c are views of exemplary components of a collapsible reservoir.
Figure 6B:
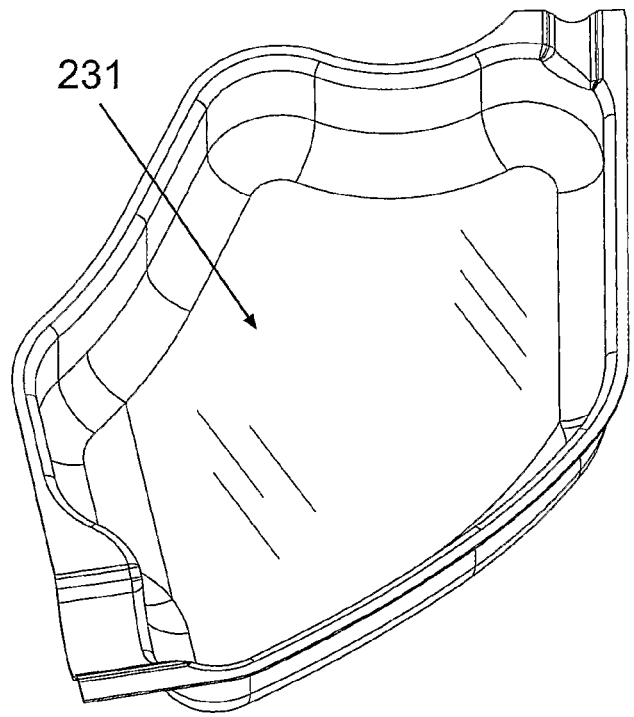
Figure 6C:
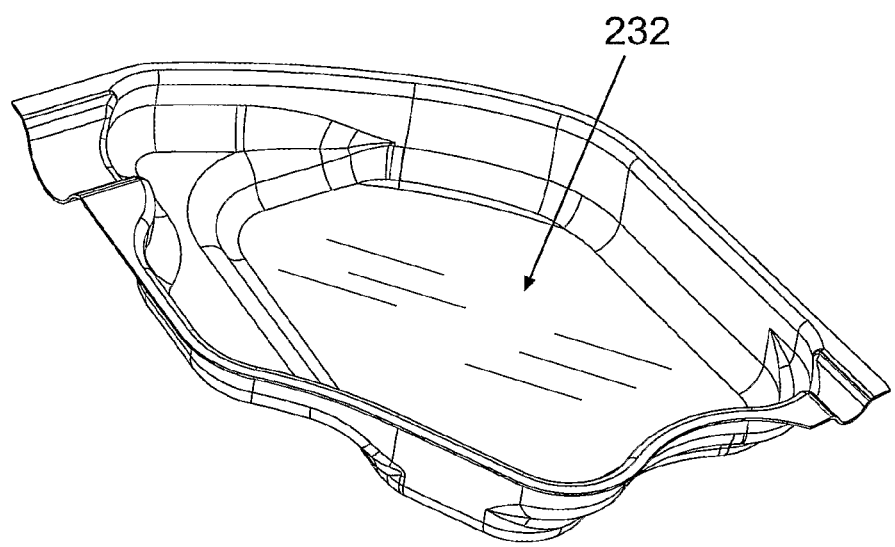

Referring to FIGS. 6a-c, views of an exemplary embodiment of a collapsible reservoir 220, including views of the reservoirs external geometry, are shown. In some embodiments, the reservoir has an irregular, amorphous, geometry with rounded corners, with a radius of curvature that, in some embodiments is between 1 and 1.4 mm. The reservoir's irregular, amorphous shape is such that the reservoir (or reservoir's shell) is adapted to fit within any housing having a volume at least equal to a volume occupied by the reservoir when the varying inner volume is at the maximum volume. As shown, the reservoir 220 includes two portions: an upper portion 231 and a lower portion 232. The two portions may be connected by welding them together. In this embodiment, the reservoir's geometry is structured so as to prevent (or reduce) entrapment of air within the reservoir while filling it with fluid, thus enabling the inner volume of the reservoir 220 to be filled with therapeutic fluid such that few, if any, pockets of air form.

Additionally, the reservoir's geometry and structure is shaped such that during fluid filling and priming, the entire volume of the reservoir is first filled before any fluid can exit through the outlet port 260. During fluid filling and priming the reservoir (and its containing unit) is held such that the outlet port is at the highest point of the reservoir. Thus, in accordance with, for example, Pascal's law the internal volume of the reservoir is filled before spillage of the fluid through the outlet port. In some embodiments the outlet port is located in a narrow portion of the reservoir, thus during the filling operation the wider portion of the reservoir is filled slowly, reducing the formation of air pockets and bubbles. The narrow portion (near the outlet port) is generally filled more quickly, and thus if air bubbles were created they would be washed out during the priming. In some embodiments the reservoir includes rounded corners, and/or having a curved shape, preferably without angles. The rounded corners significantly reduce the amount of air bubbles/pockets as air is usually trapped in angled corners, in which the interface between the two phases is reduced.

In some embodiments, the reservoir, comprising a pliable shell, has a fixed, predefined maximum volume, so that it can hold an amount of fluid that is not larger than its fixed volume. The collapsible reservoir may be constructed to be of any desired fixed volume. Thus, if, for example, the fluid to be held in the varying inner volume defined by the reservoir is insulin, and the required daily dose for kids and toddlers (e.g., 10-20 IU/day) is substantially lower than that for adults (e.g., 40-60 IU/day), then, to avoid insulin waste, the volume of the insulin reservoir (100 IU=1 ml) for usage duration of, e.g., 3 days, should be up to 1 ml for kids, and up to 3 ml for adults. In some embodiments, the varying inner volume defined by the shell of the collapsible reservoir is associated with a minimum residual volume corresponding to a minimum volume that can be reached by the pliable shell as the fluid is removed from the varying inner volume.

The amorphous shape of the collapsible reservoir described herein conforms to the shape and structure of the dispensing patch housing and is adaptable to fit in the available space within the dispensing patch housing. The adaptability feature of the collapsible reservoir enables substantial reduction of unoccupied space within the dispensing patch and/or enables minimization of the overall patch size.

In some embodiments, the reservoir may have a transparent portion through which of the therapeutic fluid inside the reservoir may be visible, thus enabling viewing of the volume (e.g., the level) of fluid present within the reservoir.

Figure 7A:
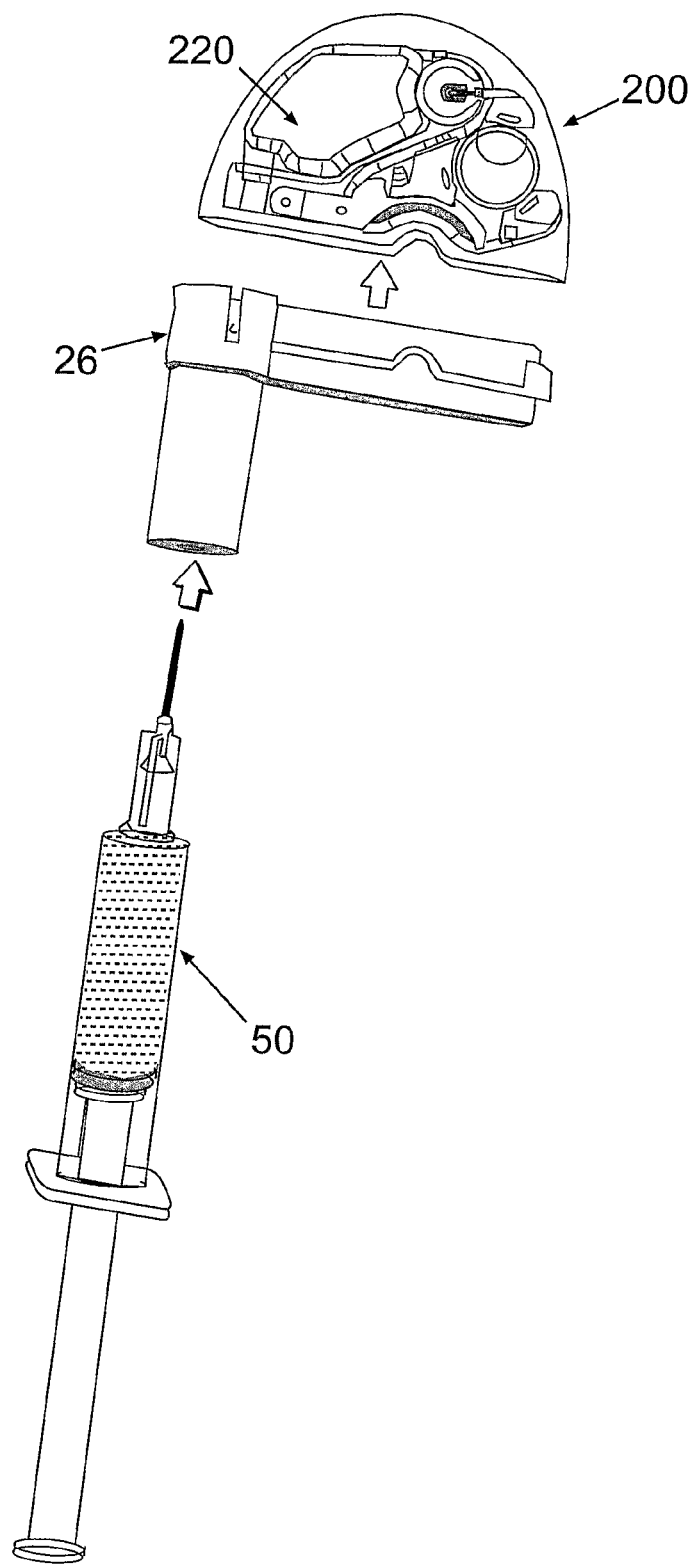
FIGS. 7a-f are views and diagrams of a reservoir of an exemplary dispensing unit being filled and primed using an adapter.

Referring to FIGS. 7a-f, exemplary views and diagrams of the collapsible reservoir 220 being filled and primed using an adapter 26 are shown. Referring to FIG. 7a, a user couples a prefilled syringe 50 to an adapter 26 connected to the disposable part 200. The adapter 26 can be connected and removed to and from the disposable part 200 as required. In some embodiments the adapter can be provided attached to a syringe.

Figure 7B:
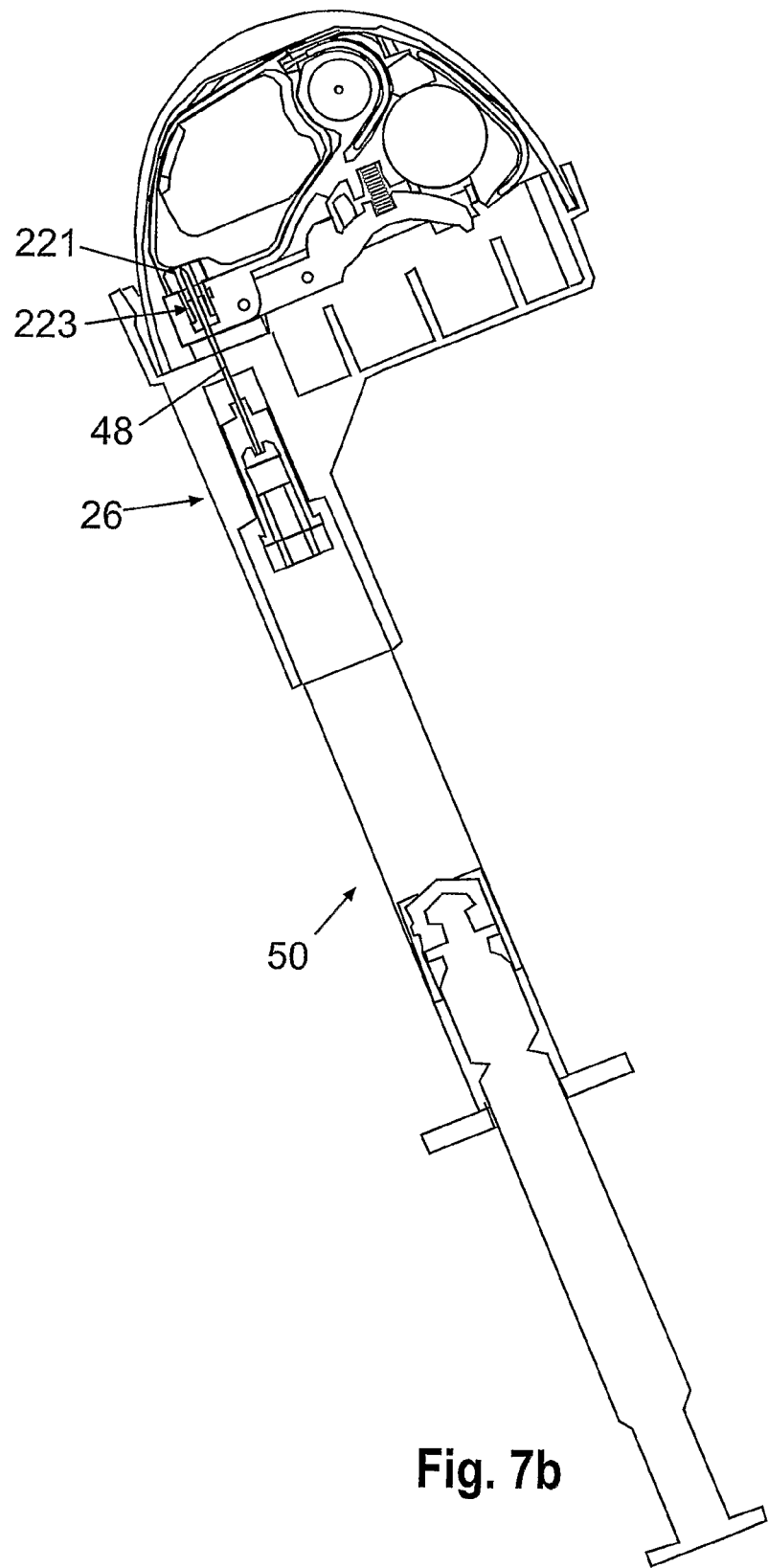

Referring to FIG. 7b, a schematic diagram of the disposable part 200, adapter 26 and syringe 50 is shown. The filled syringe 50 is connected to the filling port 221 of the reservoir 220 via the adapter 26. The needle 48 of the syringe 50 pierces the reservoir septum 223, at which point the user filling the reservoir 220 may inject fluid 290 (as shown, for example, in FIGS. 7d and 7e) from the syringe 50 into the reservoir 220.

Figure 7C:
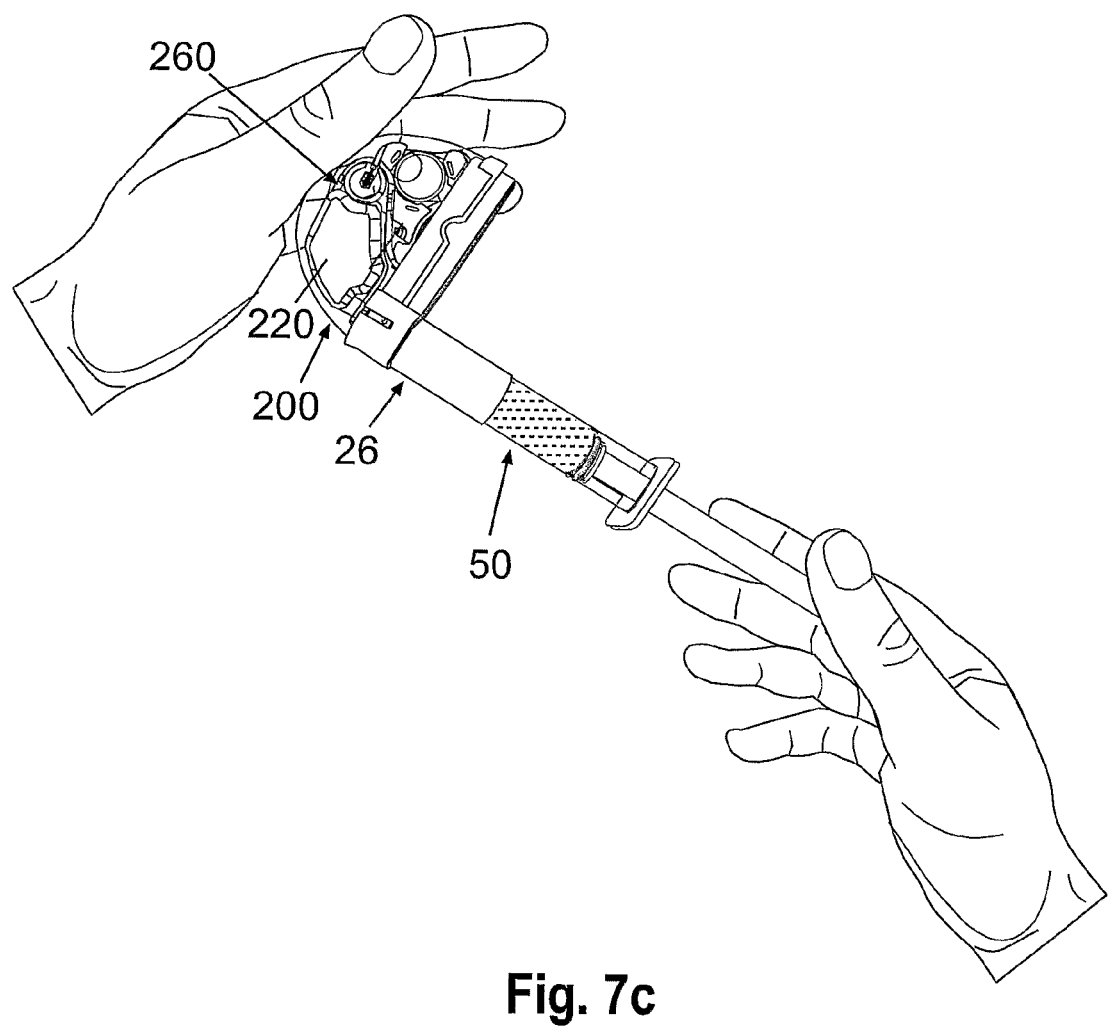

In some embodiments, during the filling operation, the user may position the disposable part 200 in an upright position, such that the reservoir outlet port 260 (as shown, for example, in FIG. 7c) is directed upwards. During filling in the upright position, the fluid entirely displaces the reservoir residual air, which exits through the reservoir outlet port 260 to thus minimize or altogether avoid trapping of air bubbles. FIG. 7c depicts the filling process using the adapter 26 and the syringe 50, where the disposable part 200 and the reservoir 220 are substantially in the upright position.

Figure 7D:
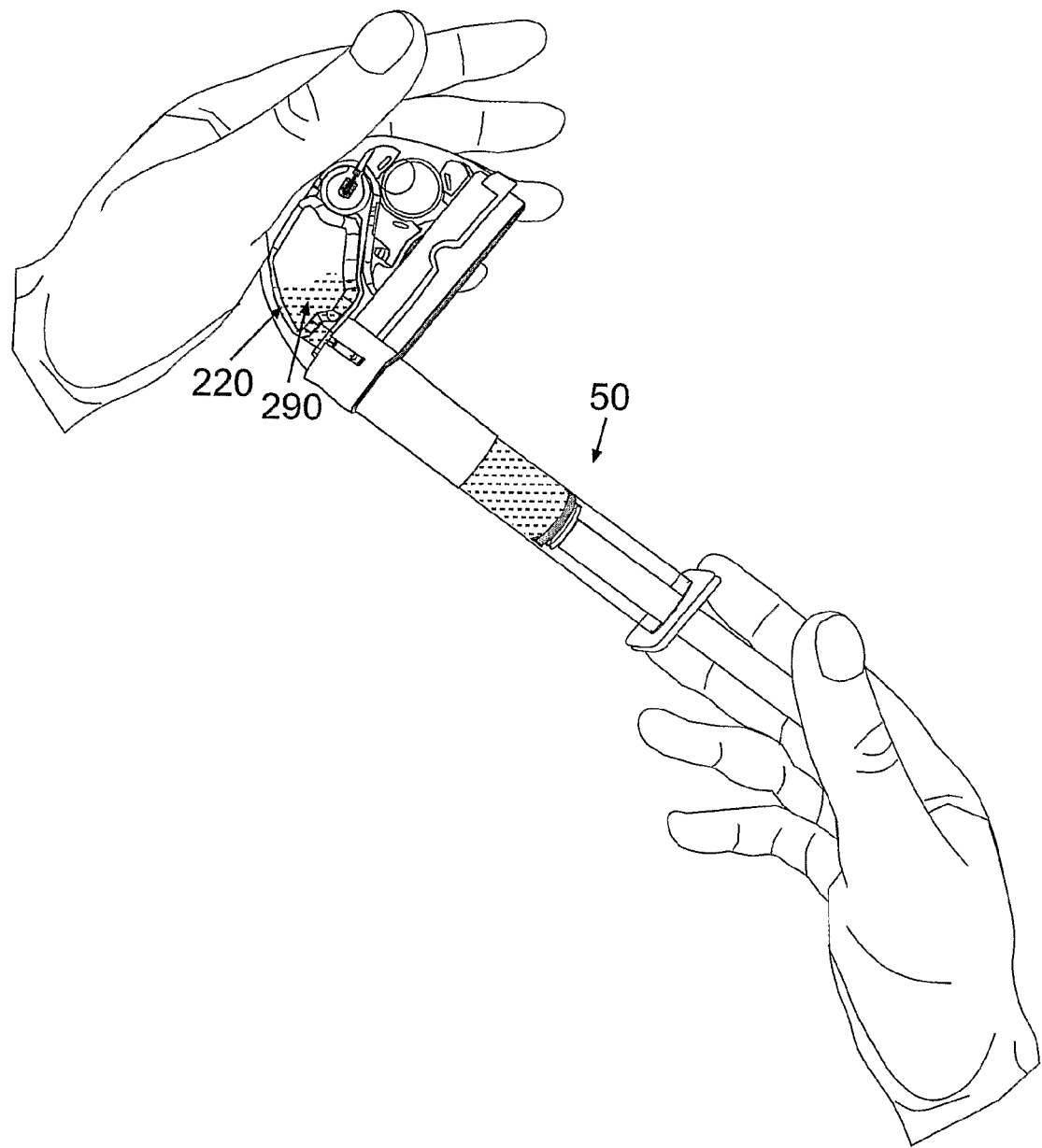
Figure 7E:
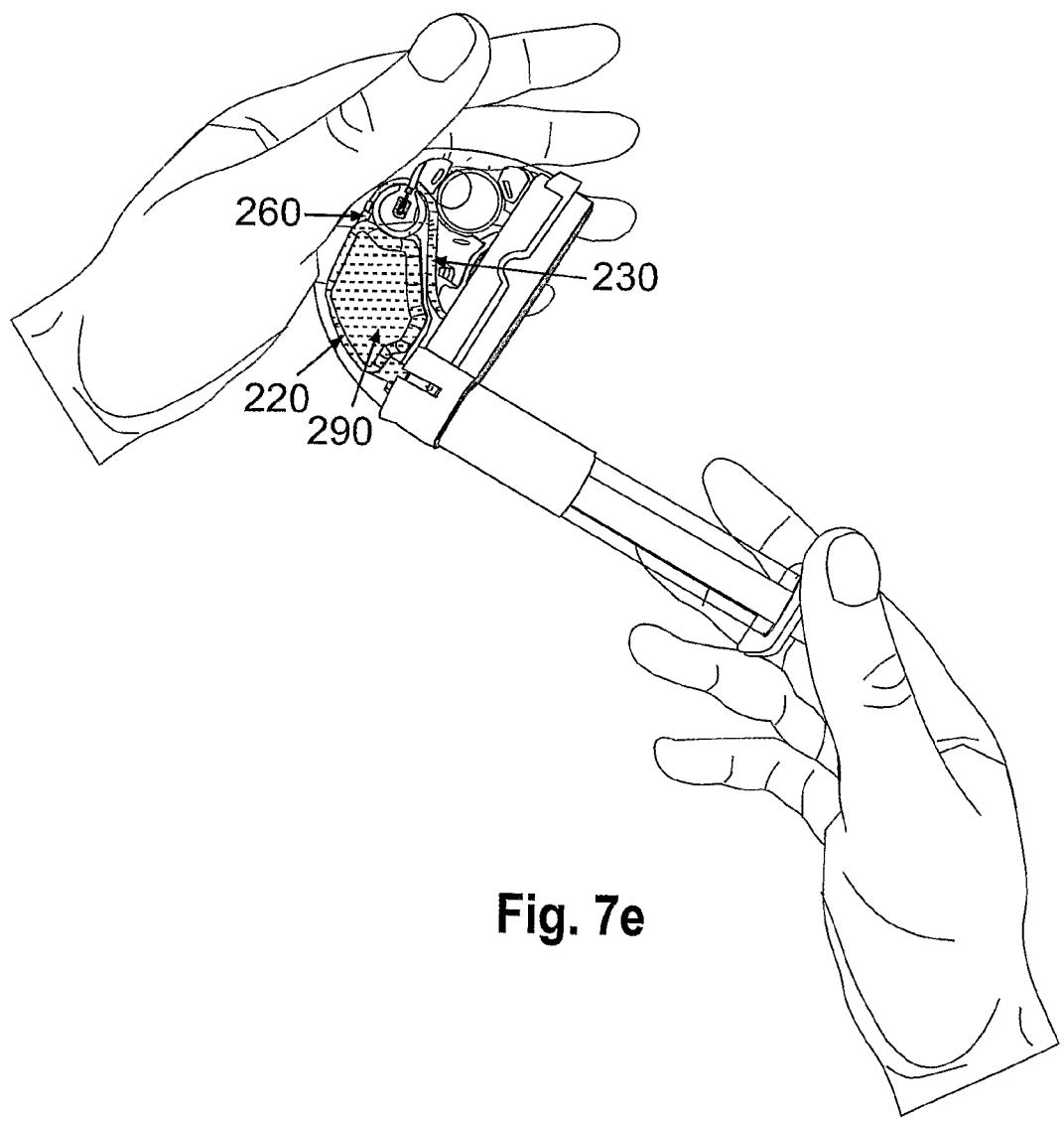
Figure 7F:
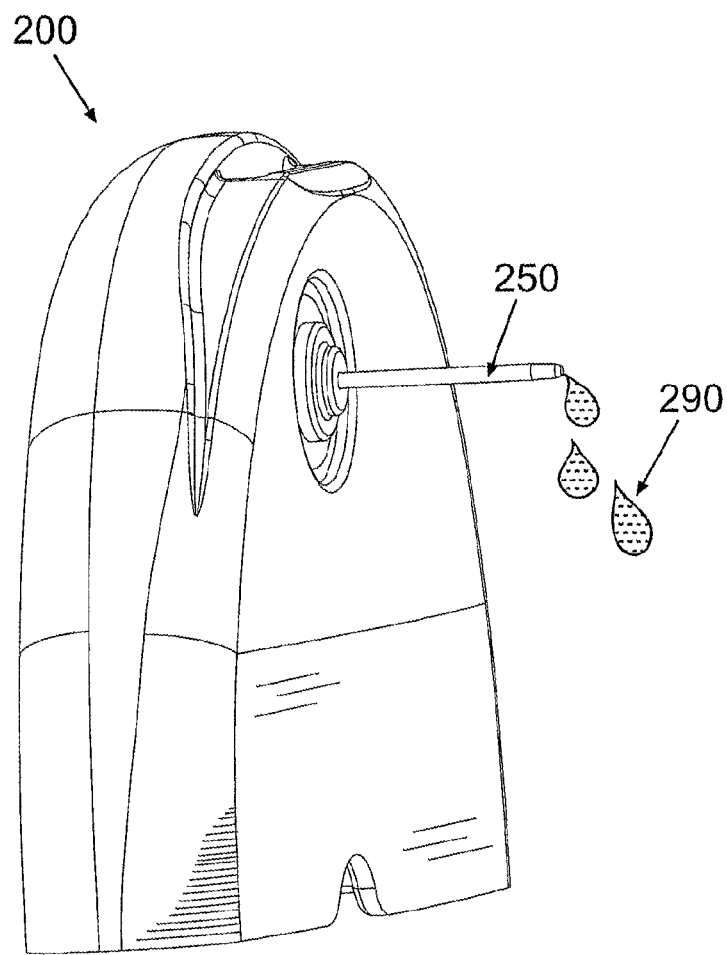

FIGS. 7d-e depict the filling and priming process. As shown in FIG. 7d, the fluid 290 enters the reservoir 220 until it is completely full (as shown in FIG. 7e). As the fluid 290 fills up substantially the entire volume of the reservoir, some of the fluid starts exiting the reservoir through the reservoir outlet port 260, fills the delivery tube 230, and eventually some drops of fluid 290 emerge from the connecting lumen 250, located at the end of the delivery tube 230, as shown in FIG. 7f.

Examples of syringe and reservoir connections using an adapter are described in greater detail, for example, in commonly-owned U.S. Ser. No. 11/989,680, filed Aug. 18, 2006, entitled "Methods and devices for delivering fluid to a reservoir of a fluid delivery device", the content of which is hereby incorporated by reference in its entirety.

Referring to FIGS. 8a-e, views and diagrams depicting the collapsible characteristic of an exemplary collapsible reservoir 220 are shown. The collapsibility of the reservoir 220 is enabled, among other reasons, due to the very thin reservoir walls, the wall material, and the material's moisture vapor transmission rate (MVTR).

Before collapsing, e.g., due to the evacuation of therapeutic fluid, the reservoir, comprising a pliable shell defining a varying inner volume, maintains its shape and structure given to it during the production process. Because the reservoir 220 is air-tight, no air enters the reservoir during fluid emptying and thus the structure of the reservoir 220 is altered to compensate for the displaced fluid 290. During fluid evacuation (e.g., as fluid is being dispensed into the user's body), suction of the fluid out of the reservoir, caused, for example, by the pumping action, causes the collapse of the reservoir, i.e., the contraction of the fluid volume in the reservoir which also result in a contraction of the reservoir itself and consequently a reduction of the reservoir's inner volume. During the evacuation of the fluid and the commensurate contraction of the collapsible reservoir, the reservoir is configured to remain air-tight.

In some embodiments, the reservoir walls are made of a non-resilient polymer. The collapsibility of the reservoir 220 is enabled due to its very thin wall, which, in some embodiments, has a thickness of less than 100 μm. In some embodiments, the walls of the collapsible reservoir have a thickness of between 80 and 100 μm.

Additionally, the reservoir's thin wall is adapted to serve as a barrier against fluid vapor and is chemically inert to the absorption of fluid constituents (e.g. water, m-cresol, phenol), as indicated by the wall material's relatively low Moisture Vapor Transmission Rate (MVTR). Generally, MVTR is a measure of the passage of water vapor through a material. When packaging substances that are sensitive to moisture loss, e.g., pharmaceutical preparations or foodstuffs, a relatively low MVTR is critical in achieving the desired quality and safety for the products. The conditions (e.g., temperature, humidity, etc.) under which the measurement is made have a considerable influence on the result. Generally, the MVTR for a reservoir, with surface area A and wall thickness t, that contains fluid of volume V and density ρ, is calculated according to the formula:

$$MTVR = \frac{V\rho t}{AT} [\text{gr} - \text{mm/m}^2/\text{day}]$$

For example, to keep 2 ml of fluid within a reservoir with wall thickness t and surface area 1000 mine, for three (3) days, with a 1% allowed loss of fluid, the MVTR is computed according to:

$$\frac{V\rho t}{AT} = 0.01 = \frac{2[\text{cm}^3] \times 1\left[\frac{\text{gr}}{\text{cm}^3}\right] t}{1000[\text{mm}^2] \times 3[\text{day}]} = 6.7 \cdot t \frac{\text{gr} \cdot \text{mm}}{\text{m}^3 \text{day}}$$

Thus, the thickness of the reservoir walls should be at least the MVTR of the reservoir's wall divided by 6.7 to enable maximum of 1% loss of fluid. Alternatively and/or additionally, the materials constituting the reservoir wall may be chosen according to their MVTR and the desired wall thickness, t.

The wall material, thickness and MVTR all contribute to the reservoir 220 ability to collapse. Full collapsibility of the reservoir would enable the entire fluid within a reservoir (such as the reservoir 220) to be almost completely depleted.

In the embodiments depicted in FIGS. 8a-f, both the upper portion 231 and the lower portion 232 of the shell constituting the reservoir collapse inward as fluid 290 is displaced from the reservoir 220 through the cannula 330 and into the body of the user. When the entire therapeutic fluid volume 290 is depleted, the reservoir 220 is completely collapsed, leaving minimal residual volume.

In some embodiments, the residual volume in the reservoir is less than 10% of the total reservoir volume. In some embodiments, the residual volume in the reservoir is less than 5%. In some embodiments, the residual volume in the reservoir is less than 0.5% of the total reservoir volume. Thus, for example, if the total volume is 2 ml (corresponding to approximately 200 IU of insulin) the residual volume would occupy a volume corresponding to the volume occupied by less than 20 IU of insulin.

Figure 8A:
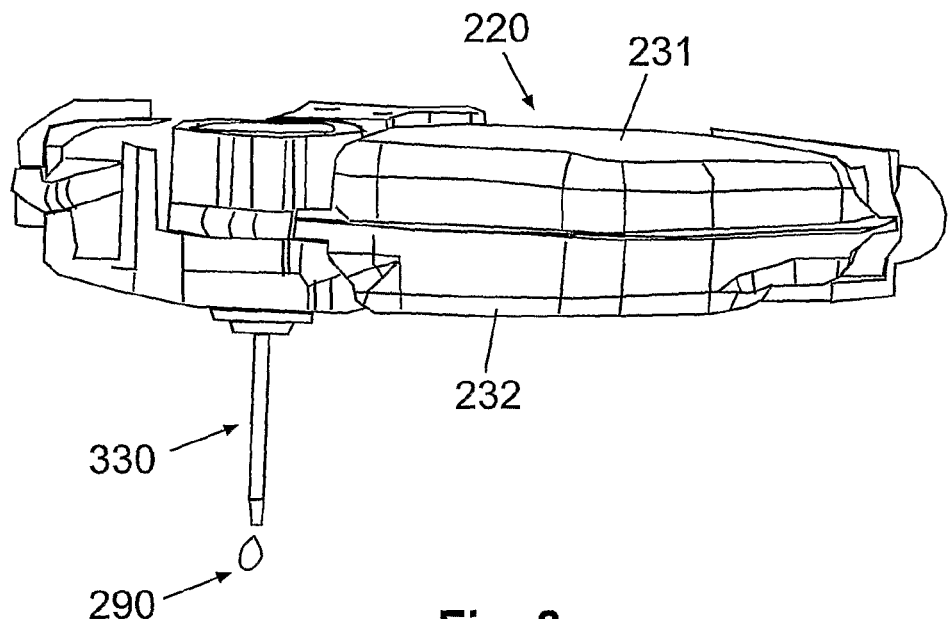
FIGS. 8a-f are views and diagrams illustrating the collapsible property of an exemplary collapsible reservoir.
Figure 8B:
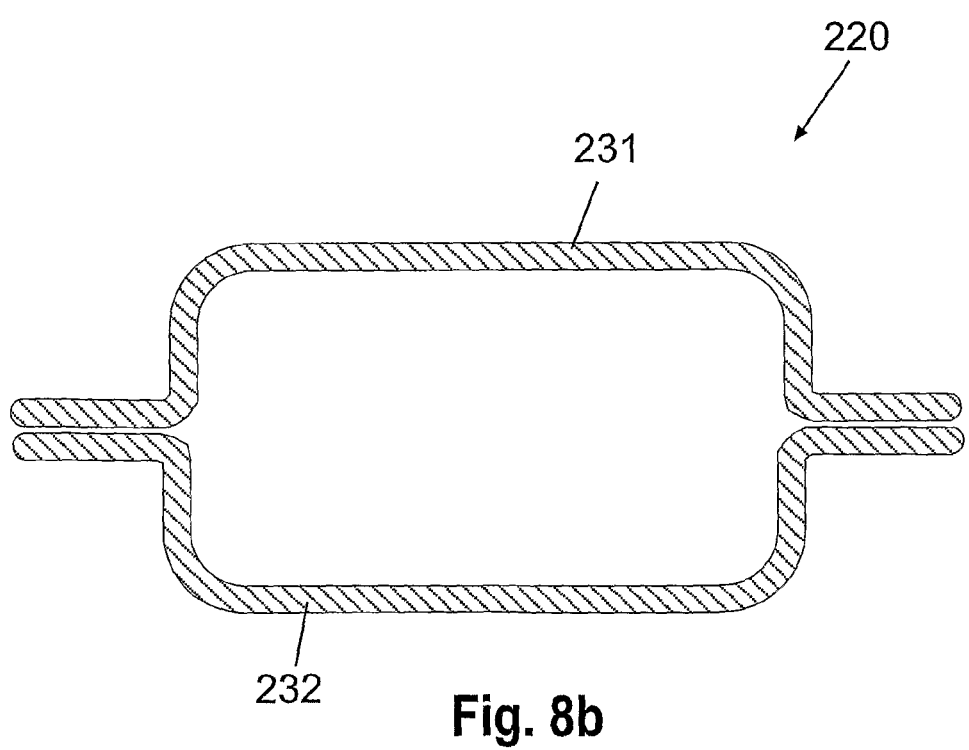

FIGS. 8a and 8b are a side perspective and cross-section views, respectively, of the collapsible reservoir 220. When the fluid 290 exits the reservoir 220, the two portions 231, 232 collapse inwardly.

Figure 8C:
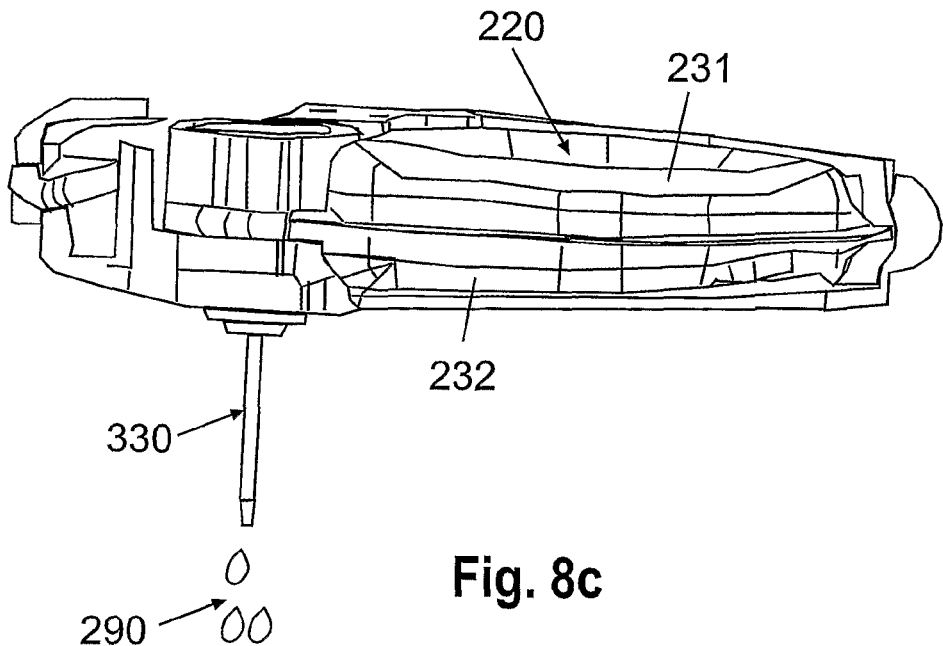
Figure 8D:
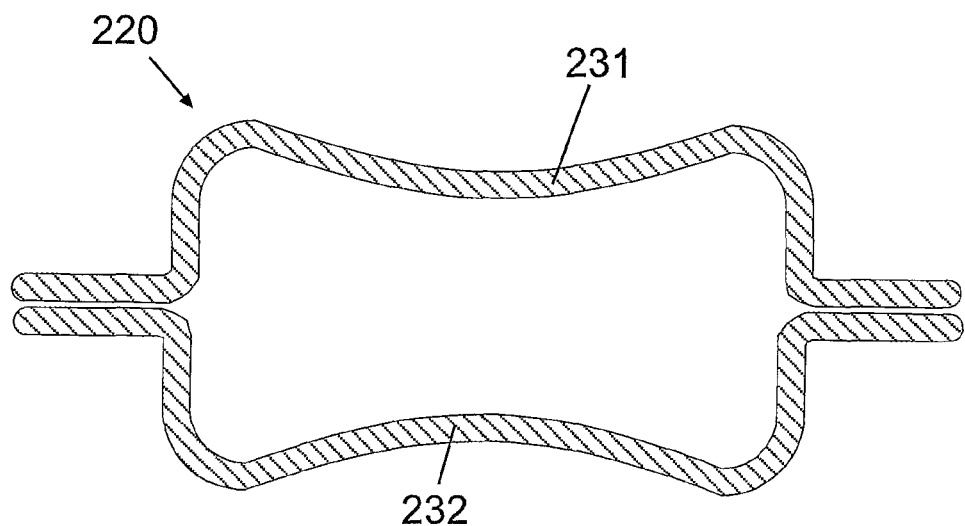

FIGS. 8c and 8d are side perspective and cross-sectional schematic views, respectively, of the exemplary collapsible reservoir 220 when fluid 290 is being evacuated from the reservoir (e.g., as the fluid is delivered into the body) through the cannula 330.

Figure 8E:
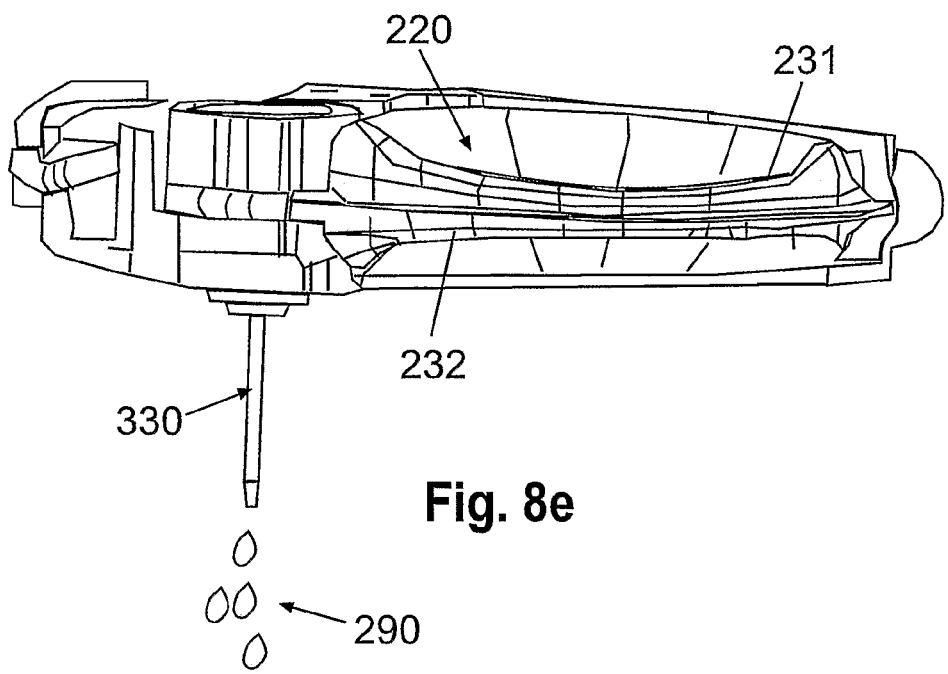
Figure 8F:
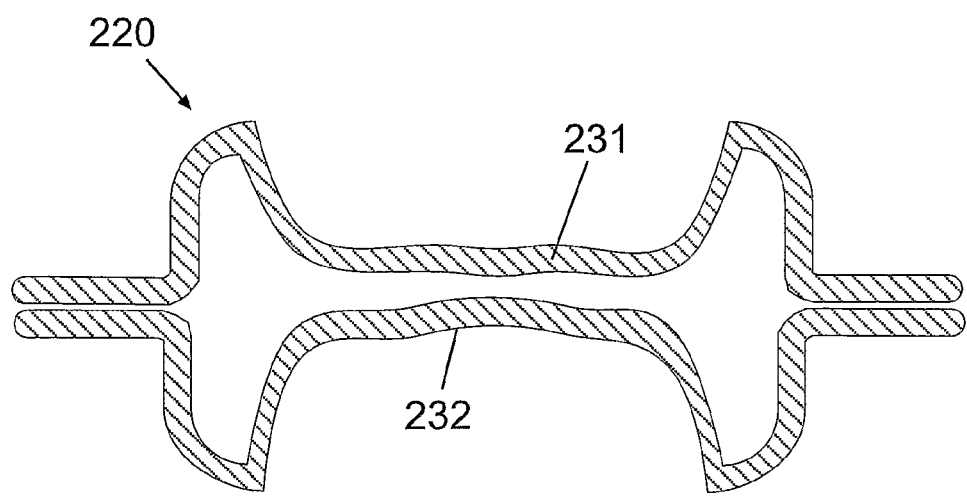

FIGS. 8e and 8f are side perspective and cross-sectional schematic views, respectively, of the exemplary reservoir 220 when all, or substantially all fluid 290 has been delivered via the cannula 330 into the patient's body. The reservoir 220 is depicted in its fully collapsible state in which the upper portion 231 and lower portion 232 of the collapsible reservoir 220 are in near contact with each other.

A collapsible reservoir may require air pressure equilibration between the interior of the patch and the ambient air to avoid restriction of collapsibility. Pressure equilibration enables the reservoir to collapse during fluid emptying and/or altitude change.

Figure 9A:
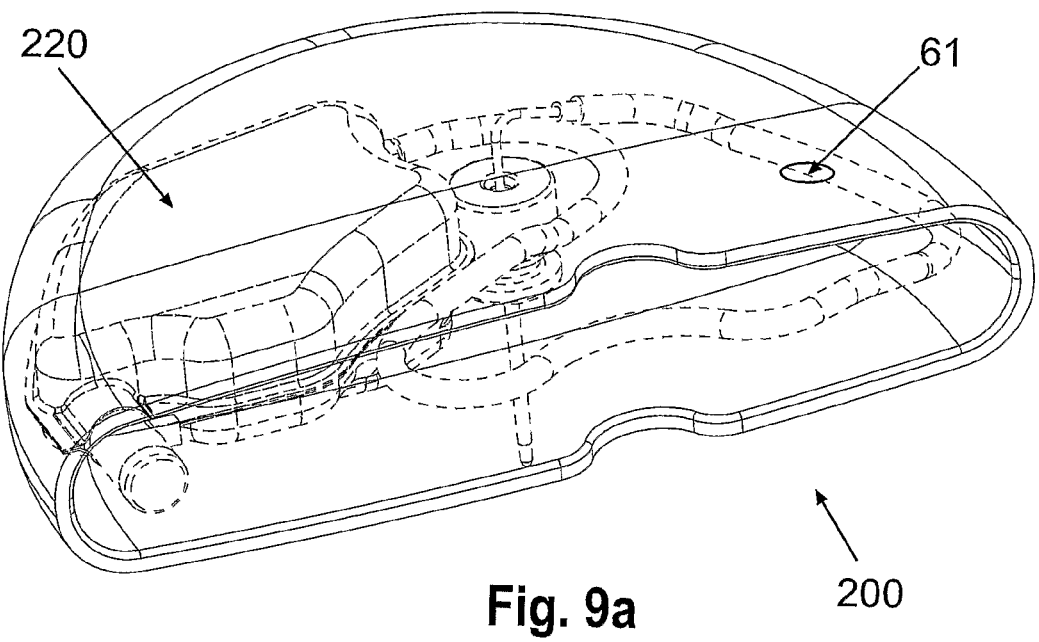
FIGS. 9a and 9b are views of exemplary disposable unit that is configured to be vented using an aperture and a selective membrane.
Figure 9B:
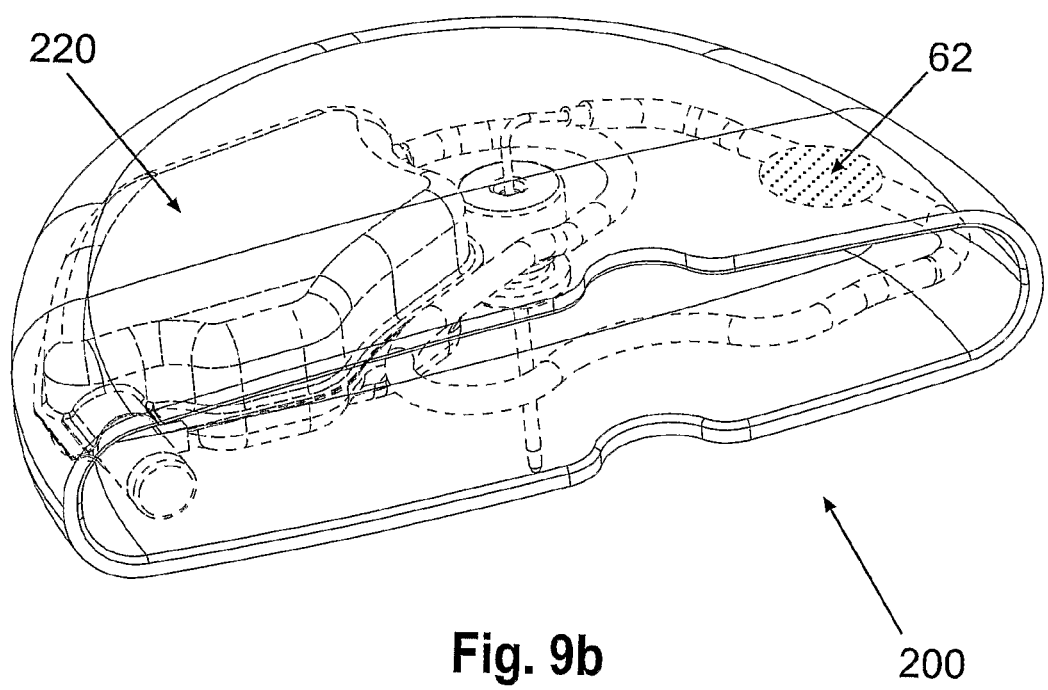

Referring to FIGS. 9a and 9b, views of an exemplary disposable part 200 configured to be vented using an aperture and/or a selective membrane are shown. The venting mechanisms enable air pressure equilibration to be established between the patch and the surrounding ambient air.

As shown in FIG. 9a, the venting mechanism includes an aperture 61 placed within the disposable part 200 housing. The aperture 61 enables entrance of air into the patch. The aperture 61 may be sealed by a seal tab (not shown) when the user comes in contact with water in order to keep the patch water proof.

As shown in FIG. 9b, a selective membrane 62 is placed within the disposable part 200 housing. The selective membrane 62, also referred to as semi-permeable membrane, has a selective permeability to prevent entry of water and/or aqueous solutions into the disposable part 200, yet enables the entrance of air into the disposable part. The membrane 62 may be made from waterproof materials and/or waterproof fabrics, including waterproof/breathable fabrics that provide gas diffusion through the membrane 62 but prevent water, moisture and/or other aqueous solutions from permeating through the membrane. An example of such a fabric is GORE-TEX™, described, for example, in U.S. Pat. No. 4,194,041, the content of which is hereby incorporate by reference in its entirety.

In some embodiments, a collapsible reservoir 220 may be biocompatible and may maintain chemical and preservative stability of the drug contained within the reservoir. Insulin, for example, tends to adhere to polymeric surfaces (Diabetes Technol Ther 2006; 8(5):521-2) and its phenolic preservatives m-cresol, phenol and other alcoholic derivatives tend to evaporate. As mentioned above, a fully collapsible reservoir requires very thin walls. Thus, in some embodiments, a collapsible reservoir to store insulin may be constructed using, for example, a multi-layered polymer film to enable maintain the chemical stability and/or formulation of the insulin drug in the reservoir.

In circumstances in which the therapeutic fluid to be held by the collapsible reservoir is insulin, the inner layer of the reservoir wall material may be, for example, PP, polyethylene, since insulin does not adhere to the surfaces of these materials. The specifications for the outer and/or middle layers are in accordance with the barrier properties of the polymer. For example, ethylene vinyl alcohol (EVOH) has low permeability for gases while PTFE is known as a good barrier for moisture, with an MVTR=0.02 gr-mm/m$^2$/day (as indicated, for example, by K-O Encyc "Film & Sheeting", 1980, 3$^{rd}$ ed.).

Thus, the multi-layered polymer film should include one or more of the following properties:

Moisture proof (or substantially moisture proof);
Impervious or substantially impervious to fluid loss, e.g., water and preservatives, e.g., m-cresol, present in the contained fluid;
Impervious or substantially impervious to entry of gas, e.g., $CO_2$, from the surroundings into the contained fluid;
Suitable MVTR and thickness;
Mechanical properties enabling flexibility and collapsibility;
Sterilisable (e.g. gamma irradiation, steam, ethylene oxide);
Nonleachable or substantially nonleachable;
Weld capable.

Figure 10A:
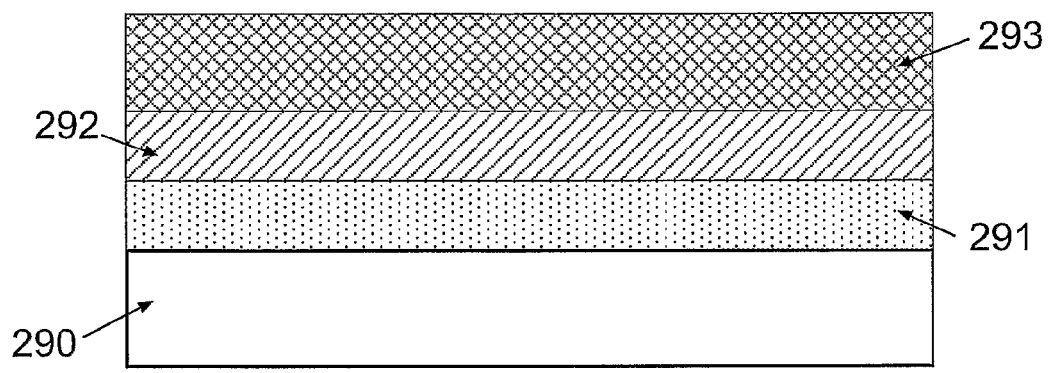
FIGS. 10a and 10b are schematic diagrams of the layered configuration of the walls of exemplary collapsible reservoirs.

Referring to FIG. 10, schematic diagrams of layered configuration of the walls of exemplary collapsible reservoirs are shown. FIG. 10a depicts a three-layered polymer film. As shown, the inner layer 291 is the layer that comes in contact with the fluid 290 within the reservoir. The inner layer 291 also serves as a barrier against moisture exiting the reservoir and can be welded. The inner layer 291 may be made of PP, which, as noted, is compatible with insulin (i.e., insulin does not significantly adhere to the surfaces of that material), non leachable (does not release substances into the fluid, i.e., the fluid does not absorbs substances from the material), preserves m-cresol and phenol (Diabet Med. 1988; 5(3):243-7, Am J Hosp Pharm 1991; 48 (12):2631-4), and is water proof. Other suitable insulin compatible polymers include polyethylene and propylene-ethylene copolymer.

The materials of the inner layer 292 is made, in some embodiments, of relatively low temperature resistant material, a property that enables welding of portions of the reservoir as will be described in greater details below. The middle layer 292 connects between the inner layer 291 and the outer layer 293 and provides flexibility and mechanical elasticity. The middle layer 292 may be made of any thermoplastic elastomer (TPE) material. The outer layer 293 is exposed to the outside environment and, in some embodiments, is made of relatively high temperature resistant PP that is not affected by welding temperature, maintains rigidity, and resists pressure overload that can occur during fluid-filling or as a result of an external impact.

In some embodiments, the three (3) layer film, depicted, for example, in FIG. 10a, has a thickness of, for example, 80 micron. The layers' materials include PP/TPE/PP and the thickness of the layers may be as follows:

Layer 1—25 µm PP low temp (to enable welding without leakage);
Layer 2—40 µm TPE (to enable flexibility); and
Layer 3—15 m PP high temp (to enable pressure resistance).

Figure 10B:
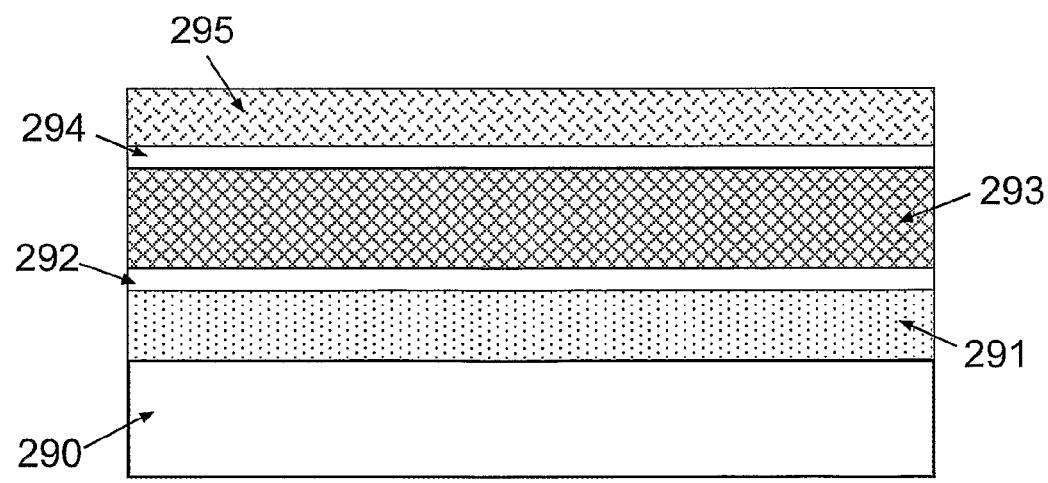

FIG. 10b shows a multi-layered polymer film comprising five or more layers. The inner 291 comes in contact with the fluid 290 within the reservoir, and thus should be compatible with the fluid 290, e.g., insulin. Here too, the inner layer 291 additionally serves as a barrier against moisture exiting the reservoir, and is further adapted to be welded. The third 293 and fifth 295 layers are, in some embodiments, made of moisture proof, and $CO_2$ proof materials, respectively. The layers may be attached to each other using a second 292 and fourth 294 adhesive layers.

Example of materials that prevent water and $CO_2$ diffusion include Polytetrafluoroethylene (PTFE), Polyvinylidenechloride (PVDC) and Ethylene vinyl alcohol copolymer (EVOH).

In some embodiments, a sixth layer (not shown) disposed on the layer 295 and thus has one surface facing the outside surrounding of the reservoir, may serve as an outer layer of the reservoir.

In some embodiments, the walls of the collapsible reservoir may be made of a single layer that be made, for example, from PP, Polyethylene or propylene-ethylene copolymer. In such embodiments, the walls are generally slightly thicker (e.g., thicker than 80 micron) to avoid evaporation, and consequently the reservoir is generally slightly more rigid than multi-layered films.

In some embodiments, the material from which the shell of the reservoir is made (be it a single-layer or multi-layer material) may be further configured to be resistant to ethylene oxide (ETO) sterilization such that characteristics of the material (e.g., strength, elasticity, etc.) do not degrade during application of ETO sterilization procedure to the shell. In some embodiments, the material may be further configured to be resistant to sterilization procedures including one or more of, for example, gamma irradiation procedure and/or steam sterilization procedure, such that characteristics of the material do not degrade during application of the sterilization procedures to the shell.

Referring to FIGS. 11 a-e, schematic diagrams of exemplary operations of a production and assembly procedure to produce/assemble a reservoir are shown. In some embodiments, production and assembly of the collapsible reservoir is performed using vacuum forming and welding processes. FIG. 11a depicts the vacuum forming stage of the procedure. As shown, a polymer film 400 is heated using, for example, a heater 55 and placed into a three-dimensional, pre-made, mold 50, shaped in the three-dimensional geometry of the two reservoir portions. The film 400 may be received into the mold by being sucked into the mold using a vacuum apparatus 51 so that the heated material of the film 400 assumes the shape of the mold 50. The molded film is subsequently removed from the mold 50 and cooled.

Figure 11A:
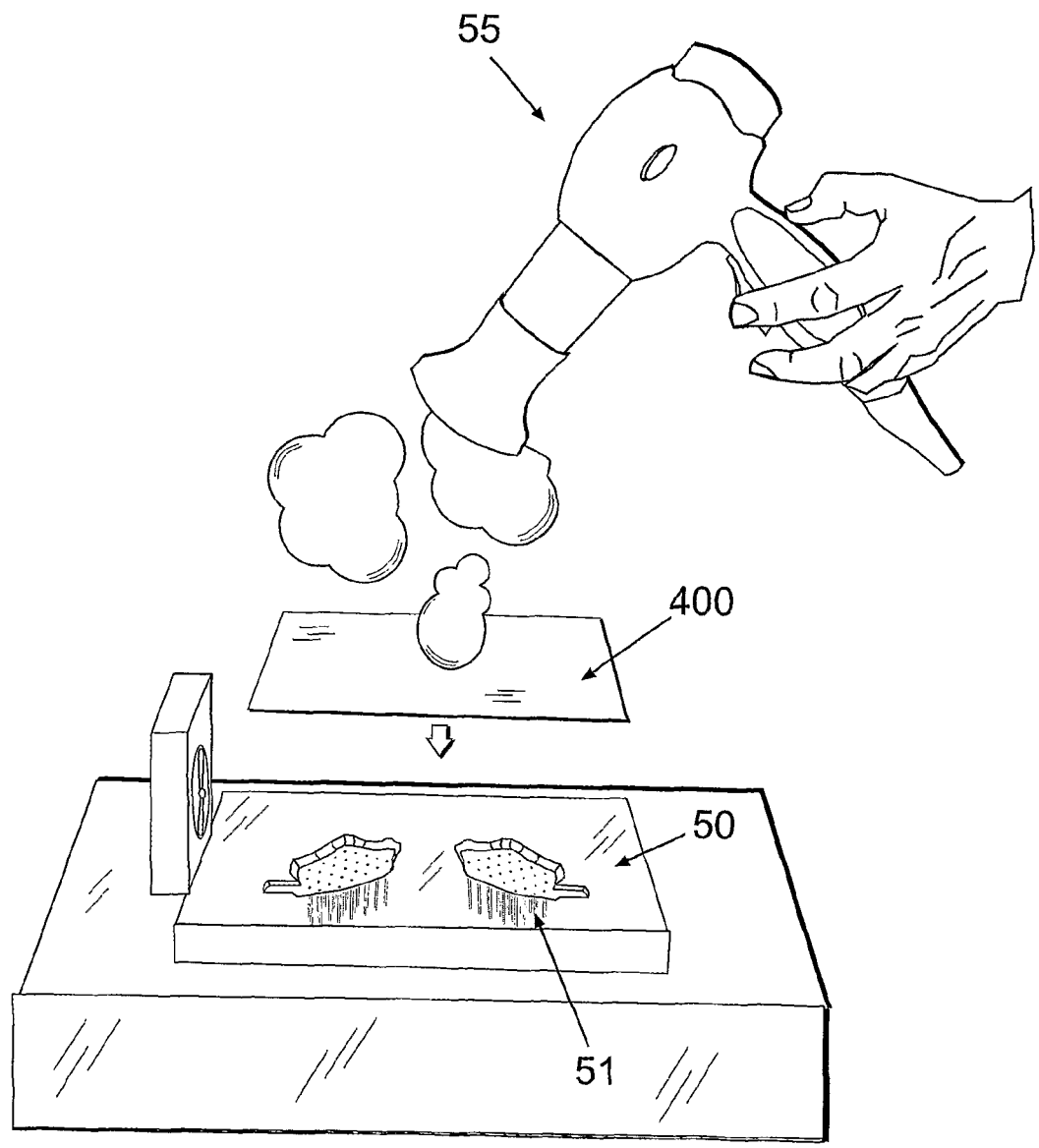
FIGS. 11a-e are schematic diagrams of exemplary operations of a production and assembly procedures to produce/assemble a reservoir.
Figure 11B:
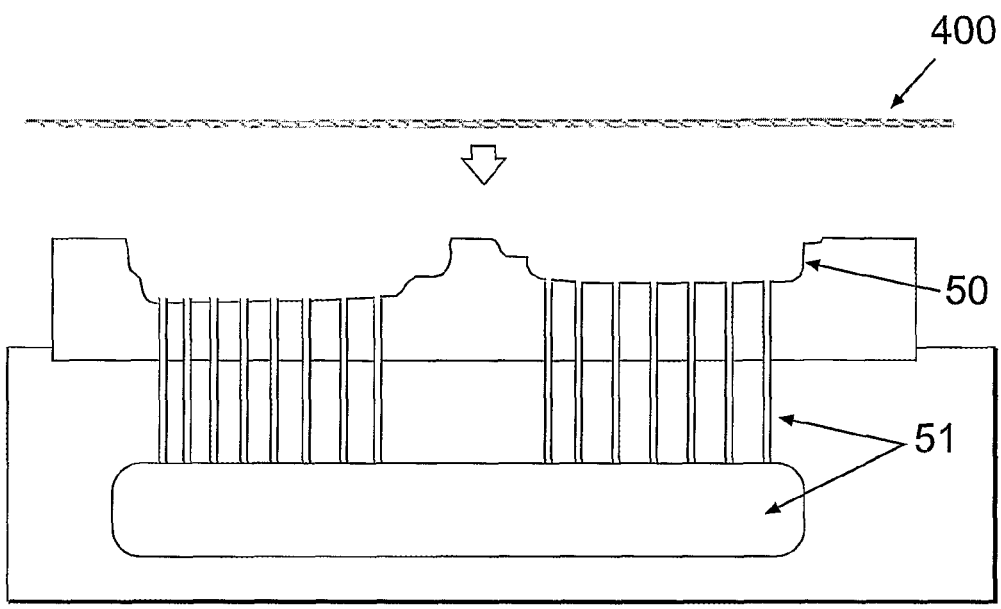
Figure 11C:
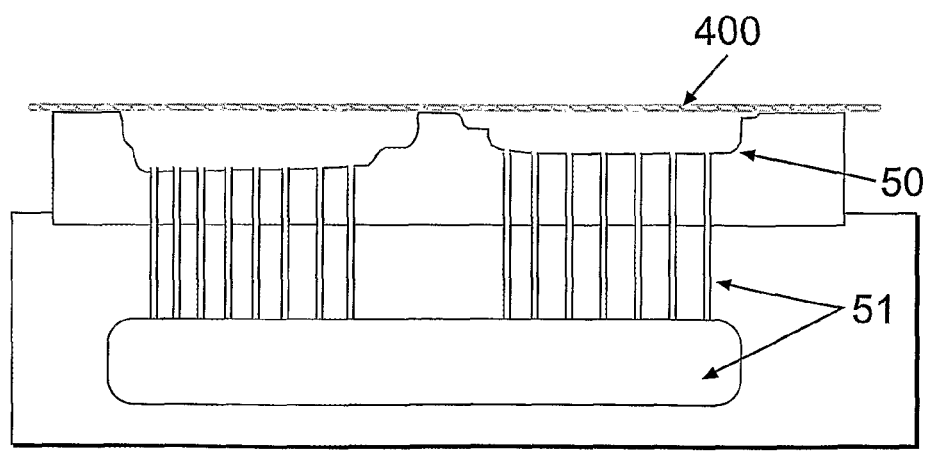
Figure 11D:
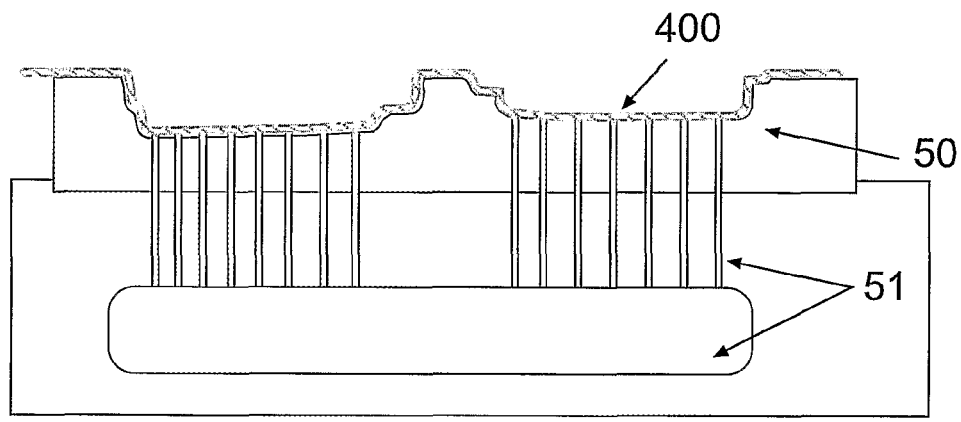
Figure 11E:
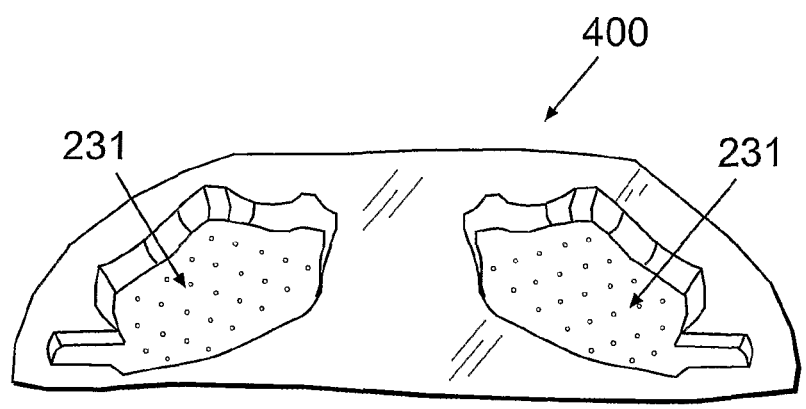

FIGS. 11b-d depict cross sections of the film 400, the mold 50, and the vacuum 51 prior to the film 400 being placed in the mold 50 and vacuum 51 assembly (as shown in FIG. 11 b); prior to commencement of the vacuum forming process (as shown in FIG. 11c); and after the placement of the film 400 into its three-dimensional shape (as shown in FIG. 11d). At the end of the vacuum forming stage, the resultant two portions of the reservoir 231 and 232 are formed, as shown in FIG. 11e.

Figure 12A:
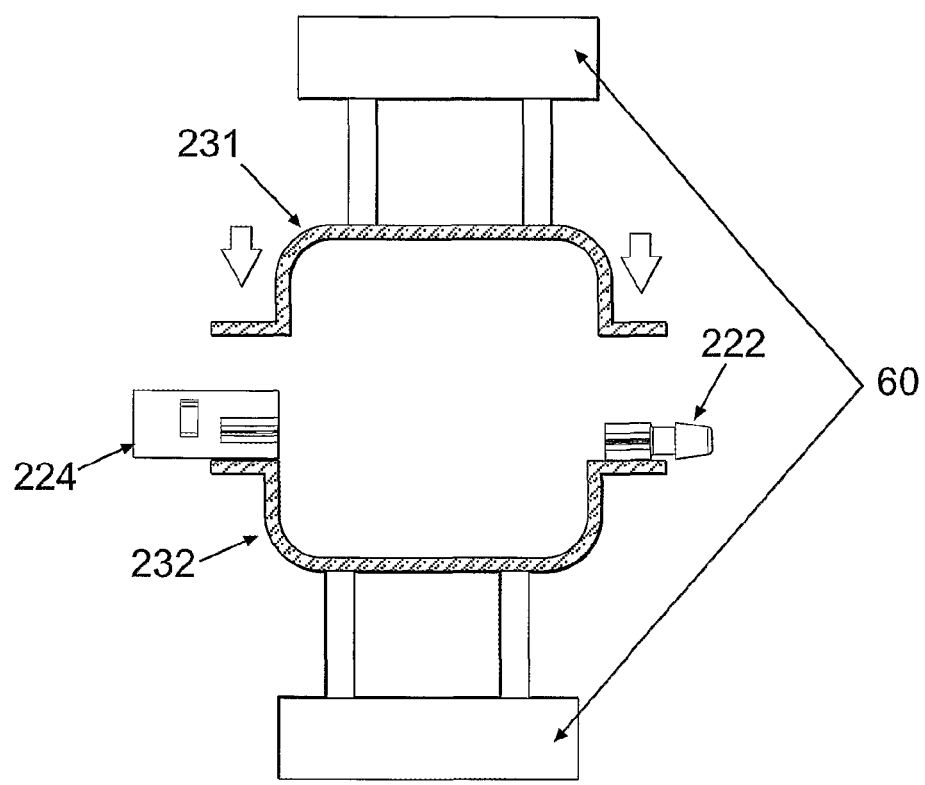
FIG. 12a-d are schematic diagrams and views depicting welding operations to weld the upper and lower portions of exemplary collapsible reservoirs.
Figure 12B:
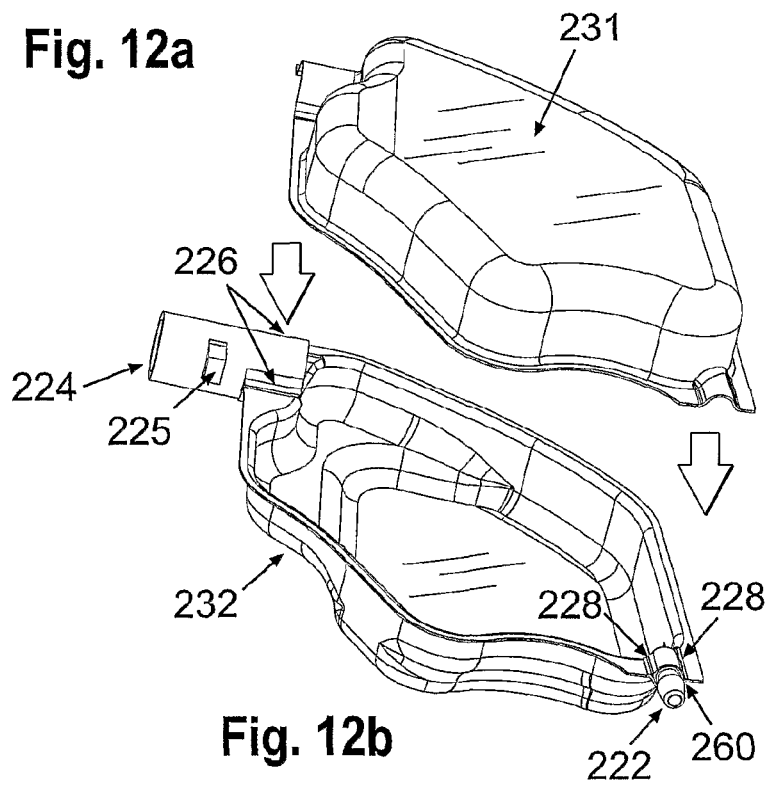

Referring to FIGS. 12a-d, schematic diagrams and views depicting welding operations to weld the upper portion 231 and lower portion 232 of the shell of the collapsible reservoir are shown. Also shown in the figures are the inlet pipe 224 and the adapter 222 that are assembled with the lower and upper portion to form the assembled collapsible reservoir. FIGS. 12a and 12b show a cross section and perspective view, respectively, of the two reservoir portions 231 and 232 prior to being welded and sealed together. Generally, the lower portion 232 is placed on the bottom part of a sealer 60, with the inlet pipe 224 and the adapter 222 placed between the lower and upper portions, typically by placing these components proximate to the two ends of the lower portion 232. As more particularly shown in FIG. 12b, the inlet pipe 224 is placed on a designated place on the lower portion 232 so that the inlet pipe's two fins 226 are positioned substantially horizontally on the lower portion 232 and the key tab 225 is facing inwards. The reservoir adapter 222 is placed on the reservoir outlet port 260 on the lower portion 232 with its two fins 228 positioned substantially horizontally on the lower portion 232. The upper portion 231 is placed on the upper part of the sealer 60, which is positioned above the lower portion 232 in the bottom part of the sealer 60.

Figure 12C:
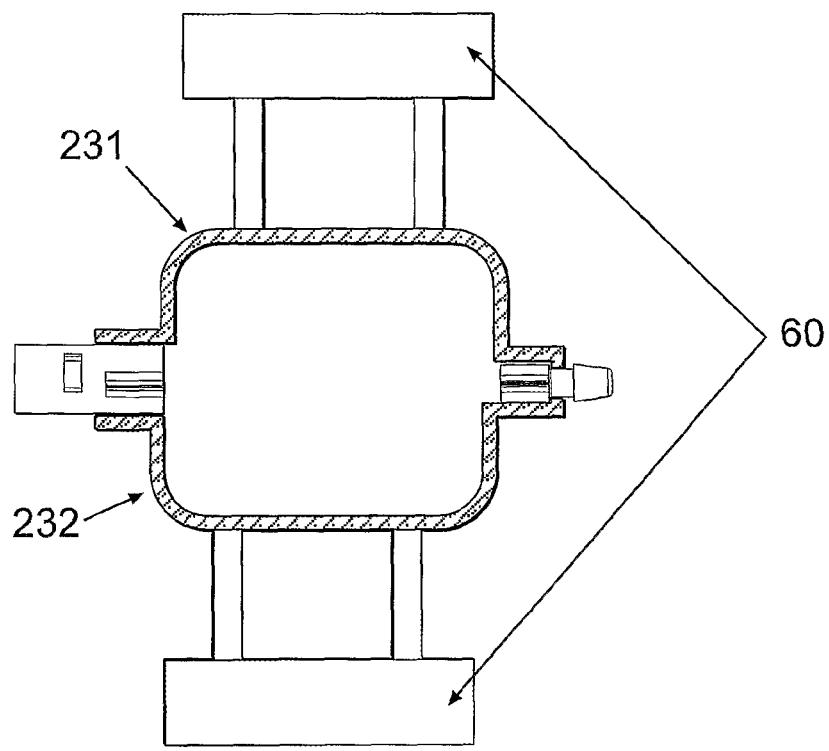
Figure 12D:
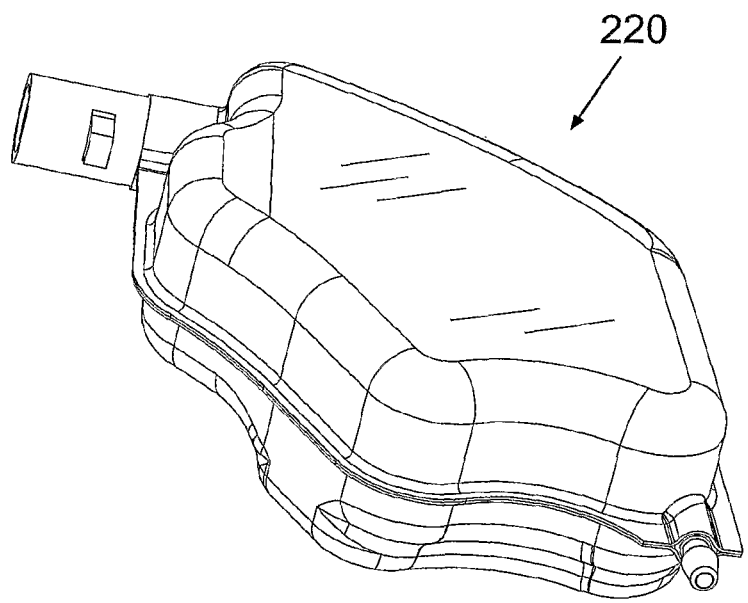

The two portions 231 and 232 are heated and pressed so they are welded together. Subsequently, the two welded portions are cooled. FIG. 12c shows a cross section of the two portions 231 and 232 still on the sealer 60, after they have been pressed together and welded. FIG. 12d shows the assembled collapsible 220 reservoir after welding processing has been completed.

Thus, a collapsible pump reservoirs and associated methods of use and manufacture have been described herein. Any and all of the foregoing patents, applications, and publications referenced in this specification are hereby incorporated by reference in their entireties. Although particular embodiments have been disclosed herein in detail, this has been done by way of example for purposes of illustration only, and is not intended to be limiting with respect to the scope of the appended claims, which follow. In particular, it is contemplated that various substitutions, alterations, and modifications may be made without departing from the spirit and scope of the invention as defined by the claims. Other aspects, advantages, and modifications are considered to be within the scope of the following claims. The claims presented are representative of the inventions disclosed herein. Other, unclaimed inventions are also contemplated.

What is claimed is:

1. An ambulatory portable dispensing device for delivering a therapeutic fluid to a patient's body, the dispensing device comprising:
   at least one housing accommodating a pump and at least a portion of a reservoir,
   at least one filling port comprising at least a self-sealable septum connectable to an inlet pipe, the inlet pipe extending out from the reservoir and comprising side fins at one end of the inlet pipe, the side fins extending within the reservoir;
   wherein the reservoir retains a therapeutic fluid for delivery to a patient's body and is configured to collapse as the therapeutic fluid is removed from the reservoir, and
   a fluid channel; and
   wherein:
      the pump is operationally coupled to the fluid channel, the operational coupling of the pump to the fluid channel removes the therapeutic fluid from the reservoir without direct force of the pump on the reservoir, and as a result of the removal of therapeutic fluid from the reservoir, the reservoir collapses from a first volume to a second smaller volume.

2. The device of claim 1, wherein the reservoir comprises:
   a pliable shell defining a varying inner volume that varies based on the volume of the therapeutic fluid retained inside the reservoir, the shell being constructed from a material configured to resist further outward expansion when the inner volume reaches a predetermined maximum volume and to contract inwardly when the fluid exits the inner volume; and
   an outlet port for communicating fluid from the reservoir to the patient, wherein any therapeutic fluid in excess of the predetermined maximum volume driven into the reservoir causes a substantially corresponding amount of therapeutic fluid to exit out of the reservoir via the outlet port.

3. The device of claim 2, wherein the shell comprises at least two portions including a first portion coupled to a second portion, such that the first portion is welded to the second portion.

4. The device of claim 2, wherein the fluid channel is configured for connection to the outlet port via an adapter, wherein the adapter is configured to receive at least a portion of the fluid channel.

5. The device of claim 2, wherein the outlet port is received within an opening defined in a narrow portion of the pliable shell, and wherein the outlet port is coupled to the pliable shell using a connector.

6. The device of claim 2, wherein the shell is constructed from a multi-layered material.

7. The reservoir of claim 6, wherein the multi-layered material comprises at least:
   an inner low temperature resistant polymer layer;
   a middle thermoplastic elastomer (TPE) layer coupled to the inner layer; and
   an outer high temperature resistant polymer layer coupled the middle layer.

8. The reservoir of claim 7, wherein the inner polymer layer is selected from the group consisting of: polypropylene, polyethylene, propylene-ethylene copolymer and combinations thereof.

9. The reservoir of claim 7, wherein the outer polymer layer is selected from the group consisting of: polypropylene, polytetrafluoroethylene (PTFE), polyvinylidenechloride (PVDC), ethylene vinyl alcohol copolymer (EVOH) and combinations thereof.

10. The reservoir of claim 7, wherein the multi-layered material further comprises one or more adhesive layers for coupling any two of the inner layer, the middle layer and the outer layer.

11. The device of claim 7, wherein the inner layer includes a thickness of about 1 µm to about 25 µm, the middle layer includes a thickness of about 2 µm to about 40 µm and the outer layer includes a thickness of about 3 µm to about 15 µm.

12. The device of claim 2, wherein the shell is constructed from a material having a thickness of less than about 100 µm.

13. The device of claim 2, wherein the shell is constructed from a material comprising a single polymer layer selected from the group consisting of: polypropylene, polyethylene, propylene-ethylene copolymer and combinations thereof.

14. The device of claim 2, wherein the shell is constructed from a material configured for resistance to one or more sterilization procedures such that characteristics of the material do not degrade during application of the sterilization procedures to the shell, such sterilization procedures including ethylene oxide (ETO) sterilization, gamma irradiation sterilization, steam sterilization procedure, and combinations thereof.

15. The device of claim 2, wherein the maximum volume of the varying inner volume is at most about 3 ml.

16. The device of claim 2, wherein the reservoir is configured to fit within any housing having a volume equal to at least a volume occupied by the shell when the varying inner volume is at the predetermined maximum volume.

17. The device of claim 2, wherein the shell includes an irregular or otherwise amorphous shape such that the shell fits within the at least one housing.

18. The device of claim 2, wherein the shell is configured with at least one curved corner such that trapping of gases and/or liquids within the varying inner volume is reduced.

19. The device of claim 1, wherein the at least one housing comprises a transparent portion through which at least part of the reservoir is visible.

20. The device of claim 1, wherein the therapeutic fluid comprises insulin.

21. The device of claim 1, wherein the pump is a peristaltic pump.

22. The device of claim 1, wherein the at least one housing is configured for securing to the patient's skin.

23. The device of claim 22, wherein the at least one housing comprises:
   a reusable part housing including the pump; and
   a disposable part housing including the reservoir.

24. The device of claim 1, wherein the at least one housing includes a vent port for air pressure equalization between an interior of the at least one housing and ambient air, wherein the vent port comprises a membrane including selective permeability enabling entry of air and substantially preventing entry of aqueous solutions into the at least one housing.

25. The device of claim 1, wherein an interior of the at least one housing includes curved corners having respective radii of curvature of between about 1 mm and about 1.4 mm.

26. The device of claim 1, wherein the pump exerts pressure on the fluid channel causing the fluid to exit the reservoir into the fluid channel.

27. The device of claim 1, wherein the fluid channel is a fluid delivery tube.

28. An ambulatory portable dispensing device for delivering a therapeutic fluid to a patient's body, the dispensing device comprising:
   at least one housing accommodating a pump and at least a portion of a reservoir,
   at least one filling port comprising at least a self-sealable septum connectable to an inlet pipe, the inlet pipe extending out from the reservoir and comprising side fins at one end of the inlet pipe, the side fins extending within the reservoir;
   wherein the reservoir retains a therapeutic fluid for delivery to a patient's body and is configured to collapse as the therapeutic fluid is removed from the reservoir, the reservoir comprises a pliable multi-layered shell defining a varying inner volume that varies based on the volume of the therapeutic fluid retained inside the reservoir, the shell is configured to resist further outward expansion when the inner volume reaches a predetermined maximum volume and to contract inwardly when the fluid exits the inner volume;
   an outlet port for communicating fluid from the reservoir to the patient, wherein any therapeutic fluid in excess of the predetermined maximum volume driven into the reservoir causes a substantially corresponding amount of therapeutic fluid to exit out of the reservoir via the outlet port;
   a vent port for air pressure equalization between an interior of the at least one housing and ambient air; and
   a fluid channel, wherein the pump is operationally coupled to the fluid channel, the operational coupling of the pump to the fluid channel removes the therapeutic fluid from the reservoir without direct force of the pump on the reservoir, and as a result of the removal of therapeutic fluid from the reservoir, the reservoir collapses from a first volume to a second smaller volume.

29. A method for communicating therapeutic fluid into a patient's body, the method comprising:
   providing an ambulatory portable dispensing device for delivering the therapeutic fluid to the patient's body, the dispensing device comprising
      at least one housing accommodating a pump and at least a portion of a reservoir,
      at least one filling port comprising at least a self-sealable septum connectable to an inlet pipe, the inlet pipe extending out from the reservoir and comprising side fins at one end of the inlet pipe, the side fins extending within the reservoir;
      wherein the reservoir retains a therapeutic fluid for delivery to a patient's body and is configured to collapse as the therapeutic fluid is removed from the reservoir; and
      a fluid channel;
   puncturing the septum of the at least one filling port; and
   operationally coupling the pump to the fluid channel, wherein the operational coupling of the pump to the fluid channel removes the therapeutic fluid from the reservoir without direct force of the pump on the reservoir, and wherein as a result of the removal of therapeutic fluid from the reservoir, the reservoir collapses from a first volume to a second smaller volume.

* * * * *